(12) United States Patent
McDonald et al.

(10) Patent No.: US 8,557,273 B2
(45) Date of Patent: Oct. 15, 2013

(54) MEDICAL DEVICES AND METHODS INCLUDING POLYMERS HAVING BIOLOGICALLY ACTIVE AGENTS THEREIN

(75) Inventors: Philip E. McDonald, Plymouth, MN (US); Kathy L. Remsen, Germantown, TN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 12/410,151

(22) Filed: Mar. 24, 2009

(65) Prior Publication Data

US 2009/0263460 A1 Oct. 22, 2009

Related U.S. Application Data

(60) Provisional application No. 61/046,213, filed on Apr. 18, 2008.

(51) Int. Cl.
*A61K 9/00* (2006.01)
*A61P 19/00* (2006.01)
*A61P 29/00* (2006.01)

(52) U.S. Cl.
USPC .......................................... 424/426; 514/401

(58) Field of Classification Search
None
See application file for complete search history.

(56) References Cited

U.S. PATENT DOCUMENTS

| | | | |
|---|---|---|---|
| 3,190,802 A | 6/1965 | Zeile et al. | |
| 3,020,660 A | 8/1965 | Zeile et al. | |
| 4,765,974 A | 8/1988 | Tokuda et al. | |
| 5,175,052 A | 12/1992 | Tokuda et al. | |
| 5,368,859 A * | 11/1994 | Dunn et al. | 424/426 |
| 5,447,947 A | 9/1995 | Campbell | |
| 5,484,607 A | 1/1996 | Horacek | |
| 5,635,204 A | 6/1997 | Gevirtz et al. | |
| 5,801,188 A | 9/1998 | Hassenbusch, III et al. | |
| 5,869,100 A | 2/1999 | Horacek | |
| 5,942,503 A | 8/1999 | Jung et al. | |
| 5,942,530 A | 8/1999 | Panetta et al. | |
| 5,945,416 A | 8/1999 | Shannon et al. | |
| 5,980,927 A * | 11/1999 | Nelson et al. | 424/425 |
| 6,030,642 A | 2/2000 | Horacek | |
| 6,069,129 A | 5/2000 | Sandberg et al. | |
| 6,147,102 A | 11/2000 | Borgman | |
| 6,179,862 B1 | 1/2001 | Sawhney | |
| 6,287,588 B1 | 9/2001 | Shih et al. | |
| 6,287,688 B1 | 9/2001 | Howell et al. | |
| 6,331,311 B1 | 12/2001 | Brodbeck et al. | |
| 6,417,184 B1 | 7/2002 | Ockert | |
| 6,428,804 B1 | 8/2002 | Suzuki et al. | |
| 6,461,631 B1 | 10/2002 | Dunn et al. | |
| 6,534,048 B1 | 3/2003 | Borgman | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,773,714 B2 | 8/2004 | Dunn et al. | |
| 6,992,110 B2 | 1/2006 | Kranzler et al. | |
| 7,345,065 B2 | 3/2008 | Gil et al. | |
| 7,507,398 B2 | 3/2009 | Rabinowitz et al. | |
| 7,524,812 B2 | 4/2009 | Ellis et al. | |
| 2002/0009454 A1 | 1/2002 | Boone et al. | |
| 2002/0013298 A1* | 1/2002 | Hunter | 514/113 |
| 2002/0058656 A1 | 5/2002 | Ockert | |
| 2002/0090398 A1 | 7/2002 | Dunn et al. | |
| 2002/0094998 A1 | 7/2002 | Burke et al. | |
| 2003/0022926 A1 | 1/2003 | Lavand'Homme | |
| 2004/0028726 A1 | 2/2004 | Fischer et al. | |
| 2004/0072799 A1 | 4/2004 | Li et al. | |
| 2004/0082540 A1 | 4/2004 | Hermida Ochoa | |
| 2004/0101582 A1 | 5/2004 | Wolicki | |
| 2004/0208917 A1 | 10/2004 | Fischer et al. | |
| 2004/0214793 A1 | 10/2004 | Hermida Ochoa | |
| 2004/0265364 A1 | 12/2004 | Ozturk et al. | |
| 2005/0058696 A1 | 3/2005 | Donello et al. | |
| 2005/0059744 A1 | 3/2005 | Donello et al. | |
| 2005/0079202 A1* | 4/2005 | Chen et al. | 424/426 |
| 2005/0095277 A1 | 5/2005 | Ozturk et al. | |
| 2005/0142163 A1 | 6/2005 | Hunter et al. | |

(Continued)

FOREIGN PATENT DOCUMENTS

| | | |
|---|---|---|
| WO | 03005961 A2 | 1/2003 |
| WO | 2005110362 A1 | 11/2005 |

(Continued)

OTHER PUBLICATIONS

International Search Report and Written Opinion for Application No. PCT/US2009/040916 mailed Dec. 11, 2009.

(Continued)

*Primary Examiner* — Robert A Wax
*Assistant Examiner* — Sarah Park
(74) *Attorney, Agent, or Firm* — Sorell Lenna & Schmidt LLP

(57) ABSTRACT

The implant design is a drug loaded polymer device, such as a rod, designed to control the release of a biologically active agent, such as clonidine or its derivatives, such as clonidine HCl for a prolonged period of time, such as 2 months, 3 months, 4 months, and even 4.5 months. The polymer is preferably a biodegradable polymer, such as poly(lactide-co-glycolide) or polylactic acid/polylactide. The challenge in using the HCl salt forms of drugs such as clonidine, is controlling the release of the highly water soluble drug for up to 4.5 months. It has been found that by controlling the particle size distribution of the drug powder, the drug distribution within the polymer matrix is more uniform and can be controlled. Therefore, the large aggregates, which cause rapid drug release can be eliminated.

16 Claims, 10 Drawing Sheets

(56) References Cited

U.S. PATENT DOCUMENTS

| | | |
|---|---|---|
| 2005/0177135 A1* | 8/2005 | Hildebrand et al. ....... 604/890.1 |
| 2005/0186261 A1 | 8/2005 | Avelar et al. |
| 2005/0197293 A1 | 9/2005 | Mellis et al. |
| 2005/0288620 A1 | 12/2005 | Shippert |
| 2006/0148903 A1 | 7/2006 | Burch et al. |
| 2006/0173060 A1 | 8/2006 | Chang et al. |
| 2006/0189944 A1 | 8/2006 | Campbell et al. |
| 2007/0021358 A1 | 1/2007 | Edelman et al. |
| 2007/0066864 A1 | 3/2007 | Forde |
| 2007/0104769 A1 | 5/2007 | Feng et al. |
| 2007/0156180 A1 | 7/2007 | Jaax et al. |
| 2007/0202074 A1 | 8/2007 | Shalby |
| 2007/0243225 A1 | 10/2007 | McKay |
| 2007/0243228 A1 | 10/2007 | McKay |
| 2008/0009830 A1 | 1/2008 | Fujimoto et al. |
| 2008/0038351 A1 | 2/2008 | Beals et al. |
| 2008/0075777 A1* | 3/2008 | Kennedy ...................... 424/484 |
| 2008/0091207 A1 | 4/2008 | Truckai et al. |
| 2008/0095831 A1* | 4/2008 | McGraw ....................... 424/450 |
| 2008/0152709 A1 | 6/2008 | Bortz |
| 2008/0171075 A1 | 7/2008 | Ozturk et al. |

FOREIGN PATENT DOCUMENTS

| | | | | |
|---|---|---|---|---|
| WO | WO 2005/110362 | * | 11/2005 | ............... A61K 9/00 |
| WO | 2006011915 A1 | | 2/2006 | |
| WO | 2006022611 A2 | | 3/2006 | |
| WO | 2006036280 A1 | | 4/2006 | |
| WO | WO 2006/036280 | * | 4/2006 | ............... A61K 9/00 |
| WO | 2006101540 A1 | | 9/2006 | |
| WO | 2008014066 A1 | | 1/2008 | |
| WO | 2008079868 A1 | | 7/2008 | |
| WO | 2009100441 A2 | | 8/2009 | |

OTHER PUBLICATIONS

Sean Moriarty, JD, QLT USA, Inc. Drug Delivery Platform, Atrigel, Revision Jul. 2006, Fort Collins, Colorado www.qltinc.com.

Miro, miro-gel Amorphous Hydrogel, Homepage: www.miro-verbandstoffe.de, (2008).

* cited by examiner

MEDICAL DEVICES AND METHODS INCLUDING POLYMERS HAVING BIOLOGICALLY ACTIVE AGENTS THEREIN

This application claims the benefit of the filing date of U.S. Provisional Application No. 61/046,213 filed Apr. 18, 2008, entitled "Medical Devices and Methods Including Polymers Having Biologically Active Agents Therein," which is hereby incorporated by reference thereto.

FIELD

The present invention generally relates to implantable medical devices for delivering a biologically active agent, and specifically, to a polymeric drug depot for delivering clonidine to a tissue in a subject.

The invention particularly relates, in a preferred embodiment, to a drug depot including a biodegradable polymer for delivering clonidine and methods of making.

BACKGROUND

Medical devices that can deliver biologically active agents such as drugs to a tissue are finding use in a wide variety of applications. For example, implantable medical devices (i.e., implants) that are capable of delivering drugs to an adjacent tissue can be designed to offer advantageous performance ranging from treatment of diseases to prevention of adverse reactions and/or rejection of the implant by the body. Implantable medical devices are typically designed with a profile for releasing biologically active agents at a specified rate over a desired period of time.

For some applications it is desirable that an implantable medical device be capable of a nearly constant rate of release of biologically active agent (e.g., a therapeutic agent) over a sustained period of time (i.e., sustained release). Frequently such medical devices include a solvent-based coating that may optionally include the biologically active agent, with the coating being capable of modulating and/or controlling the release profile of the biologically active agent. However, application of such solvent-based coatings can be problematic, for example, in that the solvent may have an adverse effect on the medical device, particularly when the medical device includes polymeric material that can be softened or dissolved by the solvent. Further, the solvent can also have an adverse effect on the biologically active agent itself, particularly when the biologically active agent is a protein-based drug. Moreover, damage that may occur to a coated medical device while making or using the device can adversely affect the ultimate performance of the device.

There is a continuing need for new medical devices that are capable of releasing biologically active agents, and methods of making such devices.

SUMMARY

The implant design is a drug loaded polymer device, such as a rod, designed to control the release of a biologically active agent, such as clonidine or its derivatives for a prolonged period of time, such as 2 months, 3 months, 4 months, and even 4.5 months. The polymer is preferably a biodegradable polymer, such as poly(lactide-co-glycolide) (PLGA) or polylactic acid/polylactide (PLA). Since the free base forms of some drugs, such as clonidine, cause undesirable polymer degradation upon processing due to its basicity, the HCl salt form, which is acidic, is preferred in some embodiments. The challenge in using the HCl salt forms of drugs such as clonidine, is controlling the release of the highly water soluble drug for up to 4.5 months. Microscopy analysis of numerous formulations shows that the drug agglomerates into large aggregates during the extrusion process. Additional analysis of the drug crystal size indicates a very large particle size distribution of the drug powder as received from the manufacturer. It has been found that by controlling the particle size distribution of the drug powder, the drug distribution within the polymer matrix is more uniform and can be controlled. Therefore, the large aggregates which cause rapid drug release can be eliminated.

Spray drying is one known technique to produce such small and tightly distributed particles. Such particles can be made by either spray drying the drug alone or spray drying the drug and polymer together. Other methods for producing particles with a narrow particle size distribution, such as micronization, crushing and sieving, and jet milling can also be used.

Medical devices, such as drug depots, that include a polymer having at least one biologically active agent therein are disclosed in the present application. In certain embodiments, the medical device is an implantable device (e.g., an orthopedic implant). Methods of using such medical devices to deliver a biologically active agent to a tissue are also disclosed herein.

In one aspect, the invention is directed to an implantable medical device, such as a drug depot for treating various maladies, such as pain. The device includes a biodegradable polymer and at least one biologically active agent disposed within the polymer. In some embodiments, the polymer has a molecular weight higher than 10,000 $M_n$ and is present in an amount from about 2-99% by weight. The biologically active agent is present in an amount from about 1-60% by weight, more specifically between 1-20% by weight, more specifically between 8-12% by weight, and is disposed within the composition as particles. At least 80%, and more specifically at least 90%, of the particles have a particle size between 1-100 micrometers in diameter, more specifically 5-50 micrometers in diameter, more specifically between about 10-20 micrometers in diameter.

In some embodiments, the implantable medical device provides an elution profile wherein less than 50% of the biologically active agent is eluted after 30, 40, 50, 60, and even 70 days after the implantable medical device is implanted in a subject under physiological conditions. In other embodiments, the device provides an elution profile wherein less than 80% of the biologically active agent is eluted after 20, 30, 40, 50, 60, 70, 80, 90, 100, 110 and even 120 days after the implantable medical device is implanted in a subject under physiological conditions.

In some embodiment, the biologically active agent is selected from the group consisting of clonidine, fluocinolone, dexamethasone and sulindac or derivatives thereof. In one embodiment, biologically active agent is clonidine, specifically clonidine hydrochloride, or clonidine HCl. Derivatives include where the parent biologically active agent may be modified to form an ester, amide, salt, solvate, hydrate, isomer, racemate, or other compound where an atom has been substituted.

In one embodiment, the polymer is selected from the group consisting of a poly lactide-co-glycolide, a polylactide, a polyorthoester and combinations thereof.

In one embodiment, the polymer has an amorphous morphology and the biologically active agent has a crystalline morphology.

In other certain embodiments, the medical device is a substantially cylindrically-shaped medical device. In certain preferred embodiments, the substantially cylindrically-shaped medical device is solid. As used herein, the terms "rod" and "cylinder" are used interchangeably to refer to a cylindrically shaped object, i.e., an object having a shape generated by rotating a parallel line around a fixed line. In some embodiments, a rod or cylinder can have as aspect ratio (radius divided by height) of 1, less than 1 (e.g., 0.9, 0.7, 0.5, 0.3, 0.1, 0.01, or even smaller), or greater than 1 (e.g., 1.1, 1, 5, 2, 3, 5, 10, 50, 100, or even greater). As used herein, cylindrically shaped objects are intended to encompass solid and/or hollow objects.

In another aspect, the present invention is directed to a method of making an implantable medical device, such as a drug depot. The method includes the steps of providing a biologically active agent as a powder, providing a polymer as a powder, combining the biologically active agent and polymer powders to form a powder mixture, melt mixing the powder mixture to form a melt mixture, and extruding the melt mixture to form the implantable medical device. At least 80%, specifically at least 90% of the biologically active agent particles have a particle size between 1-100 micrometers in diameter, more specifically 5-50 micrometers in diameter, more specifically between about 10-20 micrometers in diameter.

In one embodiment the biologically active agent is spray dried in order to provide a powder with a narrow particle size distribution. Spray drying includes combining the biologically active agent with a liquid carrier and spray drying the combined liquid carrier and biologically active agent under conditions sufficient to result in biologically active agent particles having an average particle size between about 1-100 micrometers in diameter, more specifically 5-50 micrometers in diameter, more specifically between about 10-20 micrometers in diameter.

In some embodiment, the biologically active agent is selected from the group consisting of clonidine, fluocinolone, dexamethasone and sulindac or derivatives thereof. In one embodiment, biologically active agent is clonidine, specifically clonidine HCl.

In one embodiment, the biologically active agent is present in the device in an amount between about 1-60% by weight, more specifically between about 1-20% by weight, and more specifically between about 8-12% by weight.

In one embodiment, the polymer is selected from the group consisting of a poly lactide-co-glycolide, a polylactide, a polyorthoester and combinations thereof.

In another aspect, the invention is directed to a method of delivering a biologically active agent to a tissue. The method includes placing a medical device described above or made by the method described above, such as a drug depot, proximate a tissue and allowing the medical device to deliver the biologically active agent to the tissue. In one embodiment, device is implanted as a rod proximate a site of pain or origination of pain (i.e., proximate a nerve). In another embodiment, multiple devices are implanted. In another embodiment, the implant(s) are placed proximate the tissue by delivery through a cannula, such as a needle.

In another aspect, the invention is directed to a drug depot. The drug depot includes at least one biodegradable polymer present in an amount from about 80-95% of the drug depot by weight and clonidine or a derivative thereof in an amount from about 5-20% of the drug depot by weight. The biodegradable polymer is selected from the group consisting of a poly lactide-co-glycolide, a polylactide, a polyorthoester and combinations thereof. The clonidine, preferably clonidine HCl is disposed within the drug depot as particles and at least 80% of the particles have a particle size between 10-20 micrometers in diameter.

In another aspect, the invention is directed to a method of making a drug depot. The method includes providing clonidine or a derivative thereof, preferably clonidine HCl as a powder, providing a polymer as a powder, combining the clonidine or derivative thereof and polymer powders to form a powder mixture, melt mixing the powder mixture to form a melt mixture and extruding the melt mixture to form the drug depot. The polymer is selected from the group consisting of a poly lactide-co-glycolide, a polylactide, a polyorthoester and combinations thereof. At least 80% of the clonidine particles have a particle size between 10-20 micrometers in diameter.

In another aspect, the invention is directed to a method of delivering a clonidine or a derivative thereof, specifically clonidine HCl, to a tissue. The method includes placing a drug depot proximate a tissue and allowing the drug depot to deliver clonidine or derivative thereof to the tissue. The drug depot includes at least one biodegradable polymer present in an amount from about 80-95% of the drug depot by weight and clonidine or a derivative thereof in an amount from about 5-20% of the drug depot by weight. The biodegradable polymer is selected from the group consisting of a poly lactide-co-glycolide, a polylactide, a polyorthoester and combinations thereof. The clonidine, preferably clonidine HCl is disposed within the drug depot as particles and at least 80% of the particles have a particle size between 10-20 micrometers in diameter. In one embodiment, less than 80% the clonidine HCl is released 100 days after the drug depot was placed proximate the tissue.

Further, the biologically active agent can be incorporated in a polymeric section of the device at a high enough concentration to allow for uniform dispersion of the biologically active agent in the polymeric section, while preventing undesirably high release rates by controlling the particle size distribution of the biologically active agent in the polymer. Further, the release profile can be tuned, for example, by controlling selection of the polymer material, properties and concentration, as well as concentration and particle size of the biologically active agent in the device or through the use of excipients as understood by those of skill in the art.

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 3a represents the formulation from Example 3 containing spray dried clonidine HCl/PLGA as described in Example 2. FIG. 3b represents the formulation from Example 3 containing spray dried clonidine HCl as described in Example 1 and PLGA ground into powder. FIG. 3c represents the formulation from Example 3 containing PLGA ground into powder and clonidine HCl used as received from the manufacturer.

FIG. 5a represents the formulation containing 5% clonidine HCl and 95% PLA, FIG. 5b represents the formulation containing 10% clonidine HCl and 90% PLA, FIG. 5c represents the formulation containing 5% clonidine HCl and 95% PLGA8515, and FIG. 5d represents the formulation containing 10% clonidine HCl and 90% PLGA8515.

DETAILED DESCRIPTION OF ILLUSTRATIVE EMBODIMENTS

Figure 1:
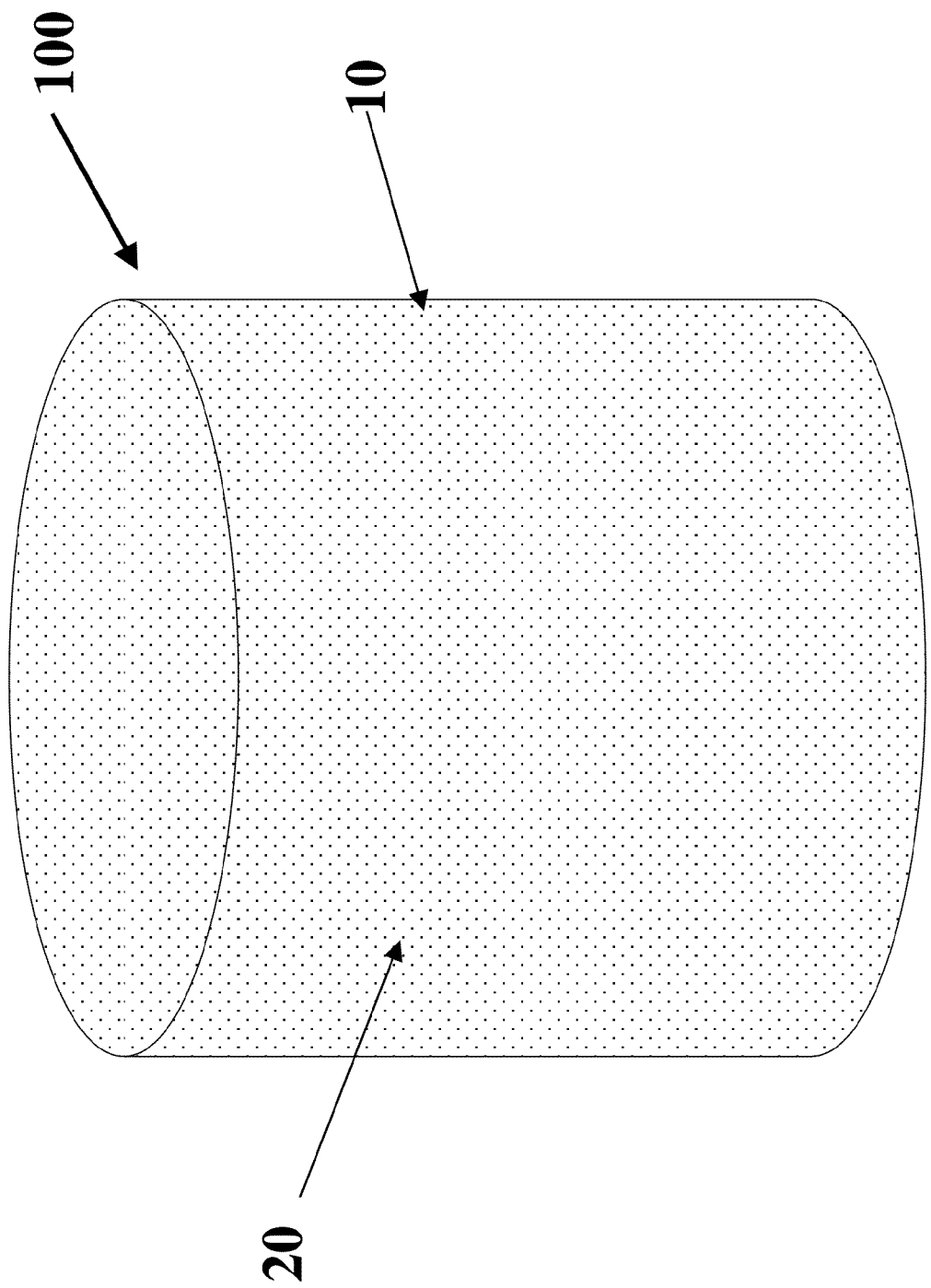
FIG. 1 is a perspective view of an embodiment of a medical device of the present invention.

One embodiment of a medical device that includes a polymer having at least one biologically active agent therein is illustrated in FIG. 1. FIG. 1 illustrates an embodiment in which medical device 100 is cylindrically shaped. However, it should be understood that medical device 100 can be any shape as desired (e.g., cube, rhomboid, cone, pyramid, sphere, ellipsoid, tetrahedron, pellet, polyhedron, other regular shapes, other irregular shapes, and the like), with the shape generally depending on the application for which the medical device is to be used. For example, cylinder shaped devices as illustrated in FIG. 1 can be used as orthopedic implants (e.g., drug depot).

Medical device 100 includes a polymer 10, and preferably an organic polymer. The polymer 10 can be a thermoplastic polymer or a thermoset polymer. The polymer 10 can be crystalline, semicrystalline, or amorphous, and is preferably amorphous.

The polymer is present in the medical device in an amount between about 2-99% by weight, more specifically, between about 20-95%, more specifically between about 50-95%, more specifically between about 60-95%, more specifically between about 70-95%, more specifically between about 80-95%, and even more specifically between about 80-90%.

In various embodiments, the medical device (e.g., drug depot) may comprise a bioabsorbable, and/or a biodegradable biopolymer that may provide immediate release, or sustained release of the bioactive agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The polymer can be porous or non-porous. As used herein, "porous" is used to refer to an object that has at least 50% void volume, preferably at least 55%, 60%, 65%, 70%, 75%, 80%, 85%, 90%, or even 95% or higher void volume. As used herein, "non-porous" is used to refer to an object that has less than 50% void volume, preferably at most 45%, 40%, 35%, 30%, 25%, 20%, 15%, 10%, 5%, or even 0% void volume. As used herein, "void volume" means unoccupied space, and percent void volume can be conveniently determined by dividing the density of the sample by the density of the fully-densified polymer.

The polymer 10 can be biostable or biodegradable. As used herein, "biodegradable" and "bioerodible" are used interchangeably and are intended to broadly encompass materials including, for example, those that tend to break down upon exposure to physiological environments. Biodegradable and/or bioerodible polymers known in the art include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)); polyanhydrides; polyketals; and poly(orthoesters).

As illustrated in FIG. 1, a biologically active agent 20 (represented by dots) is disposed within the polymer 10. The polymer is shown to hold the therapeutic agent. As used herein, the term "disposed" is intended to be broadly interpreted as inclusive of dispersed, dissolved, suspended, or otherwise contained at least partially therein or thereon.

Polymer 10 may optionally include a second biologically active agent disposed therein. The concentration of the second biologically active agent in polymer 10 can be the same as or different than the concentration of the first biologically active agent in polymer 10.

The implanted medical device provides an elution profile wherein the biologically active agent is released over a prolonged period of time. For example, less than 50% of the biologically active agent is eluted after 20, 30, 40, 50, 60, 70, 80 and even 90 days after the implantable medical device is implanted in a subject under physiological conditions. As another example, less than 80% of the biologically active agent is eluted after 20, 30, 40, 50, 60, 70, 80, 90, 100, 110 and even 120 days after the medical device is implanted in the subject.

Biologically active agents can be disposed in polymer 10 of medical devices as illustrated in FIG. 1 by a wide variety of methods. For example, devices can be formed by combining particles of a polymer and particles of at least one biologically active agent to form a mixture, and processing the mixture to provide a polymeric composite having the biologically active agent disposed therein. The biologically active agent is present in the medical device in an amount from about 1-60% by weight, more specifically between 1-20% by weight, and even more specifically between 8-12% by weight.

The polymer particles can be obtained by a wide variety of methods known to those skilled in the art. Preferably, the polymer can be ground by using liquid nitrogen to freeze the polymer and by using a mechanical milling apparatus to obtain particles of desired size. Other methods include, for example, precipitation of particles using a non-solvent for the polymer, spray drying, fluidized bed coating, hot melt precipitation, and/or other methods in which desired particle sizes can be achieved. In certain embodiments, the polymer particles have an average size of at least 10 micrometers, and preferably at least 60 micrometers. In certain embodiments, the polymer particles have an average size of at most 150 micrometers, and preferably at most 100 micrometers. As used herein, particle size refers to the diameter of spherical particles, and to the longest dimension for other shaped particles.

The biologically active agent may be provided as particles or can be ground to provide particles of the at least one biologically active agent. The particles of the biologically active agent may be obtained by a wide variety of methods known to those skilled in the art. Specific methods include, for example, mechanical manipulation (e.g. mortar and pestle, dry milling), spray drying, jet milling, lyophilization, solvent precipitation, hot melt precipitation, fluidized bed coating, micronization, and/or other methods in which a desired particle size can be achieved. In a preferred embodiment, the biologically active agent is spray dried. In certain embodiments, the particles of biologically active agent have an average size of at least 5 micrometers, and preferably at least 10 micrometers. In certain embodiments, the particles of biologically active agent have an average size of at most 50 micrometers, and preferably at most 30 micrometers. In certain embodiments, at least 60%, more specifically at least 70%, more specifically at least 80%, more specifically at least 90%, and even more specifically at least 95%, of the particles of biologically active agent are between about 1 and 100 micrometers in diameter, more specifically between about 5 and 50 micrometers in diameter, more specifically between about 10 and 50 micrometers in diameter, more specifically between about 10 and 30 micrometers in diameter and even more specifically between about 10 and 20 micrometers in diameter. In some embodiments, the biologically active agent has a particle size of about 20 to about 30 micrometers, where at least 50%, more specifically at least 70%, more specifically at least 80%, more specifically at least 90%, and even more specifically at least 95% or more specifically at least 99% of the particles are in this size range. In some embodiments, at least 50%, more specifically at least 70%, more specifically at least 80%, more specifically at least 90%, and even more specifically at least 95% or more specifically at least 99% of the particles are substantially spherical shaped or spherical shaped, such as can be accomplished by spray drying. The remaining particles may be non-spherical shaped. As used herein, substantially spherical shapes include particles that are of a smooth rounded shape that lack many projections and/or cavities on the surface. Examples of substantially spherical shapes include, but are not limited to, spherical, spheroidal, globular, round, or the like. Non-spherical shapes include irregular shaped particles that have projections and/or cavities on the surface. Such shapes include square, nearly square, rectangular, needle, rod, flake, or the like.

The medical device can also include other active ingredients, surfactants, excipients, radiopaque agents or other ingredients or combinations thereof. When there are other active ingredients, surfactants, excipients, radiopaque agents or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the medical device.

The particles of the polymer and the particles of the at least one biologically active agent can then be mixed. Preferred methods of mixing include those that do not require the use of a solvent, such as, for example, dry mixing (e.g., using a mortar and pestle). Wet mixing techniques can also be used providing that they result in a final dry mixture that is homogenous, that includes the desired particles size ranges, and that has acceptable residual solvent levels.

The mixture of particles of the polymer and the at least one biologically active agent can then be processed (e.g., fused) and formed. The mixture can be processed by heating the mixture, pressurizing the mixture, or both. Processing techniques for forming the medical device include molding techniques (for example, injection molding, rotational molding, and so forth), extrusion techniques (for example, extrusion, co-extrusion, multi-layer extrusion, and so forth) and casting. Where thermoplastic materials are employed, a melt mixture may be formed by heating the mixture of particles, which can optionally be mixed with various additives, such as excipients, to form a melt mixture. Devices in which the materials may be mixed in this fashion include devices such as single screw extruders, twin screw extruders, banbury mixers, high-speed mixers, ross kettles, and so forth.

Optionally, the mixture can be processed by introducing the mixture into a mold, which can be heated, pressurized, or both. The mixture can be heated to a temperature sufficient to melt and/or fuse the particles together.

A specific temperature that is sufficient to melt and/or fuse the particles together can be readily determined by one of skill in the art, and will commonly depend on, among other things, the characteristics of the polymer of the polymer particles including, for example, transition temperatures (e.g., glass transition temperature, $T_g$, and/or crystalline melt temperatures) and molecular weight of the polymer. For example, a temperature sufficient to melt and/or fuse the particles together can typically be 20° C. above the $T_g$ of the polymer. In a similar manner, polymer particles can be processed to provide other sections of the medical device that may or may not have biologically active agents disposed therein.

The medical device is then formed from the melt mixture. In embodiments utilizing a mold, the device is formed in the mold. In embodiments utilizing an extruder, the mixture can be extruded into any desired geometry and can then be cut to a desired length. The extruded sections can be the medical device or can be one component of the medical device which can then be combined with other components. Specifically, the mixture is extruded through a die to create a geometry, such as a cylinder, having a desired dimension with regards to diameter and length.

Alternatively, the device can be formed by methods known in the art. For example, the polymer and/or the biologically active agent can be dissolved, dispersed, or suspended in a solvent, followed by removal of the solvent, provided that the drug is not soluble in the drug.

As used herein, a "biologically active agent" is intended to be broadly interpreted as any agent capable of eliciting a response in a biological system such as, for example, living cell(s), tissue(s), organ(s), and being(s). Biologically active agents can include natural and/or synthetic agents. Thus, a biologically active agent is intended to be inclusive of any substance intended for use in the diagnosis, cure, mitigation, treatment, or prevention of disease or in the enhancement of desirable physical or mental development and conditions in a subject. The term "subject" as used herein is taken to include humans, sheep, horses, cattle, pigs, dogs, cats, rats, mice, birds, reptiles, fish, insects, arachnids, protists (e.g., protozoa), and prokaryotic bacteria. Preferably, the subject is a human or other mammal.

A preferred class of biologically active agents includes drugs. As used herein, the term "drug" means any therapeutic agent. Suitable drugs include inorganic and organic drugs, without limitation, and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems (including urological systems), histamine systems, and the like. Such conditions, as well as others, can be advantageously treated using compositions as disclosed herein.

Suitable drugs include, for example, polypeptides (which is used herein to encompass a polymer of L- or D-amino acids of any length including peptides, oligopeptides, proteins, enzymes, hormones, etc.), polynucleotides (which is used herein to encompass a polymer of nucleic acids of any length including oligonucleotides, single- and double-stranded DNA, single- and double-stranded RNA, DNA/RNA chimeras, etc.), saccharides (e.g., mono-, di-, poly-saccharides, and mucopolysaccharides), vitamins, viral agents, and other living material, radionuclides, and the like. Examples include antithrombogenic and anticoagulant agents such as heparin, coumadin, protamine, and hirudin; antimicrobial agents such as antibiotics; antineoplastic agents and antiproliferative agents such as etoposide, podophylotoxin; antiplatelet agents including aspirin and dipyridamole; antimitotics (cytotoxic agents) and antimetabolites such as methotrexate, colchicine, azathioprine, vincristine, vinblastine, fluorouracil, adriamycin, and mutamycinnucleic acids; antidiabetic such as rosiglitazone maleate; and anti-inflammatory agents. Anti-inflammatory agents for use in the present invention include glucocorticoids, their salts, and derivatives thereof, such as cortisol, cortisone, fludrocortisone, Prednisone, Prednisolone, 6α-methylprednisolone, triamcinolone, betamethasone, dexamethasone, beclomethasone, aclomethasone, amcinonide, clebethasol and clocortolone.

Preferred classes of drugs include, for example, Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof. Examples of preferred drugs are bone morphogenetic proteins (BMP) including, for example, recombinant human bone morphogenetic protein (rhBMP-2).

Suitable drugs can have a variety of uses including, but are not limited to, anticonvulsants, analgesics, antiparkinsons, antiinflammatories (e.g., ibuprofen, fenbufen, cortisone, and the like), calcium antagonists, anesthetics (e.g., benoxinate, benzocaine, procaine, and the like), antibiotics (e.g., ciprofloxacin, norfloxacin, clofoctol, and the like), antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, or the like.

Certain preferred embodiments include a drug selected from the group consisting of indomethacin, sulindac, diclofenal, etodolac, meclofenate, mefenamic acid, nambunetone, piroxicam, phenylgutazone, meloxicam, dexamethoasone, betamethasone, dipropionate, diflorsasone diacetate, clobetasol propionate, galobetasol propionate, amcinomide, beclomethasone dipropionate, fluocinomide, betamethasone valerate, triamcinolone acetonide, penicillamine, hydroxychloroquine, sulfasalazine, azathioprine, minocycline, cyclophosphamide, methotrexate, cyclosporine, leflunomide, etanercept, infliximab, ascomycin, beta-estradiol, rosiglitazone, troglitazone, pioglitazone, S-nitrosoglutathione, gliotoxin G, panepoxydone, cycloepoxydon tepoxalin, curcumin, a proteasome inhibitor (e.g., bortezomib, dipeptide boronic acid, lactacystin, bisphosphonate, zolendronate, epoxomicin), antisense c-myc, celocoxib, valdecoxib, or combinations thereof.

Certain preferred embodiments include a drug selected from the group consisting of podophyllotoxin, mycophenolic acid, teniposide, etoposide, trans-retinoic acids, 9-cis retinoic acid, 13-cis retinoic acid, rapamycin, a rapalog (e.g., Everolimus, ABT-578), camptothecin, irinotecan, topotecan, tacromilus, mithramycin, mitobronitol, thiotepa, treosulfan, estramusting, chlormethine, carmustine, lomustine, busultan, mephalan, chlorambucil, ifosfamide, cyclophosphamide, doxorubicin, epirubicin, aclarubicin, daunorubicin, mitosanthrone, bleomycin, cepecitabine, cytarabine, fludarabine, cladribine, gemtabine, 5-fluorouracil, mercaptopurine, tioguanine, vinblastine, vincristine, vindesine, vinorelbine, amsacrine, bexarotene, crisantaspase, decarbasine, hydrosycarbamide, pentostatin, carboplatin, cisplatin, oxiplatin, procarbazine, paclitaxel, docetaxel, epothilone A, epothilone B, epothilone D, baxiliximab, daclizumab, interferon alpha, interferon beta, maytansine, and combinations thereof.

Certain preferred embodiments include a drug selected from the group consisting of salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, dexamethasone, fluocinolone, ketorolac, pentoxifylline, rapamycin, ABT-578, gabapentin, baclofen, sulfasalazine, bupivacaine, sulindac, clonidine, etanercept, pegsunercept, or combinations thereof.

The headings below are not meant to limit the disclosure in any way; embodiments under any one heading may be used in conjunction with embodiments under any other heading.

Clonidine

In one embodiment, the biologically active agent comprises clonidine. When referring to clonidine, unless otherwise specified or apparent from context it is understood that the inventor is also referring to pharmaceutically acceptable salts or derivatives thereof. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Further, when referring to clonidine the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non limiting example, when formulating clonidine with poly(orthoesters) it may be desirable to use the clonidine base formulation. By contrast, when formulating clonidine with PLGA, it may be desirable to use the HCl salt form.

In one embodiment, the clonidine, is 2,6-dichloro-N-2-imidazolidinyldenebenzenamine. Clonidine or a pharmaceutically acceptable salt thereof is available from various pharmaceutical manufactures.

The dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In various embodiments, there is a pharmaceutical formulation comprising: clonidine, wherein the clonidine comprises from about 1 wt. % to about 20 wt. % of the formulation, and at least one biodegradable polymer. In some embodiments, the pharmaceutical the clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% clonidine composition, the mole ratio of clonidine to polymer would be from approximately 16-52 when using an approximately 80 kDalton polymer that has a 267 grams/mole ratio.

In some embodiments, the at least one biodegradable polymer comprises poly(lactic-co-glycolide) (PLGA) or poly (orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide;

10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, there is a pharmaceutical formulation comprising: clonidine, wherein the clonidine is in the form of a hydrochloride salt, and comprises from about 1 wt. % to about 20 wt. % of the formulation, and at least one biodegradable polymer, wherein the at least one biodegradable polymer comprises poly(lactide-co-glycolide) (or poly (lactic-co-glycolic acid)) or poly(orthoester) or a combination thereof, and said at least one biodegradable polymer comprises at least 80 wt. % of said formulation.

In some embodiments, the loading of clonidine is from about 5 wt. % to about 10 wt. %. In some embodiments, the loading is from about 10 wt. % to about 20 wt. %.

In some embodiment there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

In some embodiments, the formulations are slightly rigid with varying length, widths, diameters, etc. For example, certain formulations may have a diameter of 0.50 mm and a length of 4 mm.

In some embodiments, clonidine is released at a rate of 2-3 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 300-425 micrograms. For example, one may implant a single does of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

In some embodiments, there is a drug depot comprising clonidine or clonidine hydrochloride and a polymer, wherein the polymer is one more of various embodiments, the drug depot comprises poly(lactide-co-glycolide) (PLGA), polylactide (PLA), polyglycolide (PGA), D-lactide, D,L-lactide, L-lactide, D,L-lactide-c-caprolactone, D,L-lactide-glycolide-ε-caprolactone or a combination thereof.

When using a plurality of pellets, the pellet number is based on the amount of drug loading into a pellet of appropriate size (i.e., 0.5 mm diameter×4 mm length) and how much drug is needed (e.g., approximately 325 µg clonidine (3 pellets)). In some embodiments there is a polymer that releases a bolus amount of compound over the first few (~5) days before it settles down and releases clonidine for 135 days.

In some embodiments, the polymer depots of present application enable one to provide efficacy of the active ingredient that is equivalent to subcutaneous injections that deliver more than 2.5 times as much drug.

Fluocinolone

In one embodiment, the medical device comprises an anti-inflammatory agent, which comprises fluocinolone or a pharmaceutically acceptable salt thereof such as the acetonide salt. Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.0005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day.

Dexamethasone

In one embodiment, the medical device comprises an anti-inflammatory agent, which comprises dexamethasone free base or dexamethasone acetate, also referred to as 8S,9R,10S, 11S,13S,14S,16R,17R)-9-Fluoro-11,17-dihydroxy-17-(2-hydroxyacetyl)-10,13,16-trimethyl-6,7,8,11,12,14,15,16 octahydrocyclopenta[a]-phenanthren-3-one), or a pharmaceutically acceptable salt thereof, which is available from various manufacturers.

In various embodiments, dexamethasone may be released from the depot at a dose of about 10 pg to about 80 mg/day, about 2.4 ng/day to about 50 mg/day, about 50 ng/day to about 2.5 mg/day, about 250 ng/day to about 250 ug/day, about 250 ng/day to about 50 ug/day, about 250 ng/day to about 25 ug/day, about 250 ng/day to about 1 ug/day, about 300 ng/day to about 750 ng/day or about 0.50 ug/day. In various embodiments, the dose may be about 0.01 to about 10 µg/day or about 1 ng to about 120 µg/day.

In one exemplary embodiment, the dexamethasone is dexamethasone sodium phosphate.

GED

In one embodiment, the medical device comprises a therapeutic agent, which is GED (guanidinoethyldisulfide), which is an inducible nitric oxide synthase inhibitor having anti-inflammatory properties. GED may be in its hydrogen carbonate salt form.

The dosage of GED may be from approximately 0.0005 µg/day to approximately 100 mg/day. Additional dosages of GED include from approximately 0.0005 µg/day to approximately 50 mg/day; approximately 0.0005 µg/day to approximately 10 mg/day; approximately 0.0005 µg/day to approximately 1 mg/day; approximately 0.0005 to approximately 800 µg/day; approximately 0.0005 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; and approximately 0.0025 to approximately 15 µg/day. In another embodiment, the dosage of GED is from approximately 0.005 to approximately 15 µg/day. In another embodiment, the dosage of GED is from approximately 0.005 to approximately 10 µg/day. In another embodiment, the dosage of GED is from approximately 0.005 to approximately 5 µg/day. In another embodiment, the dosage of GED is from approximately 0.005 to 2.5 µg/day. In some embodiments, the amount of GED is between 40 and 600 µg/day. In some embodiments, the amount of GED is between 200 and 400 µg/day.

In one exemplary embodiment the dosage of GED is between 0.5 and 4 mg/day. In another exemplary embodiment the dosage of GED is between 0.75 and 3.5 mg/day.

Lovastatin

In one embodiment, the medical device comprises an anti-inflammatory agent, which comprises lovastatin. Lovastatin is a statin that may be obtained from various manufacturers in various forms (e.g., injection, powder, etc.). For example, lovastatin may be obtained from Merck as Mevacor® (see U.S. Pat. No. 4,231,938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of lovastatin include lithium, calcium, hemicalcium, sodium, potassium, magnesium, aluminum, ferrous or ferric salts thereof or a combination thereof.

In various embodiments, the therapeutically effective amount of lovastatin comprises from about 0.1 pg to about 2000 mg, for example, 0.1 ng to 1000 mg, 500 mg, 100 mg, 50 mg, 25 mg, 10 mg, 1 mg, 50 µg, 25 µg, 10 µg, 1 µg, 500 ng, 250 ng, 100 ng, 75 ng, 50 ng, 25 ng, 15 ng, 10 ng, 5 ng, or 1 ng of lovastatin per day. In various embodiments, the dosage may be, for example from about 3 ng/day to 0.3 µg/day.

Morphine

In one embodiment, the medical device comprises an analgesic, which comprises morphine. Morphine is also referred to as (5α,6α)-7,8-didehydro-4,5-epoxy-17-methylmorphinan-3,6-diol and has the chemical formula $C_{17}H_{19}NO_3$. Morphine and a pharmaceutically acceptable salt thereof is available from various manufacturers. In one exemplary embodiment, the morphine comprises morphine sulfate or hydrochloride.

The dosage of the morphine may be from 0.1 mg to 1000 mg per day. For example, the dosage of morphine may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg of morphine per day.

Tramadol

In one embodiment, the medical device comprises an analgesic, which comprises tramadol. Tramadol is also referred to as (±)cis-2-[(dimethylamino)methyl]-1-(3-methoxyphenyl)cyclohexanol hydrochloride and has the chemical formula $C_{16}H_{25}NO_2$. Tramadol or a pharmaceutically acceptable salt thereof is available from various manufacturers. In various embodiments, tramadol HCL was used.

The dosage of the tramadol may be from 0.01 mg to 500 mg per day. For example, the dosage of tramadol may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, or 500 mg of tramadol per day.

In one embodiment, the drug depot contains sufficient tramadol to release between 2.5 and 30 mg/kg/day. In another embodiment the drug depot contains sufficient tramadol to release between 3 and 27.5 mg/kg/day.

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the formulation.

In various embodiments, the medical device (e.g., drug depot) may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect.

The drug can be crystalline, semi-crystalline or amorphous, preferably crystalline.

Medical devices (e.g., implantable medical devices) can be prepared using a wide variety of polymers. Preferred polymers include, but are not limited to, polyurethanes (e.g., polyether urethanes, polyester urethanes, and polycaprolactone urethanes), polyureas, polyurethane-ureas, polyesters (e.g., polyethylene terephthalate), polycarbonates, poly(meth)acrylates, polysulfones, polyimides, polyamides, epoxies, polyacetals, polyketals, poly(orthoesters), vinyl polymers, polyanhydrides, polytriazoles, silicone rubber, natural rubber, rubber latex, synthetic rubbers, polyether-polyamide block copolymers, polyester-polyether copolymers, and combinations and/or copolymers thereof. Exemplary polyesters include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)). Polyethylene glycol homopolymers and copolymers can also be used alone or in conjunction with any of the polymers described above.

In various embodiments, the molecular weight of the polymer can be a wide range of values. The average molecular weight of the polymer can be from about 10,000 to about 1,000,000; or about 20,000 to about 500,000; or about 50,000 to about 500,000; or about 50,000 to about 200,000; or about 50,000 to 100,000.

In determining which biologically active agents and polymers to use, several factors regarding compatibility and activity should be considered. For example, hydrophilic agents tend to release quickly in aqueous environments and hydrophobic agents tend to release slowly if at all. However, some desired hydrophobic forms of drugs degrade the polymers during processing due to their basic nature, thus requiring agents be used in a hydrophilic form in order to be processed with the polymer. Clonidine, for example, is hydrophobic in its base form, but hydrophilic in salt forms such as clonidine HCL. Thus, when using a degradable polymer system that is sensitive to bassicity, it may be preferable to use the hydrophilic form of the agent to avoid prematurely degrading the polymer during processing. Some polymers degrade in acidic or basic environments and compatibility with certain agents may be affected. For example, polyorthoesters tend to degrade in acidic environments (pH lower than 7), and PLGA tends to degrade in basic environments (pH higher than 9) as well as highly acidic environments (pH less than about 4). Thus, when utilizing an agent such as clonidine HCl, which is slightly acidic (pH about 5), it may be preferable to use PLGA to avoid premature degradation of the polymer during processing.

The implantable medical device, such as a drug depot, can be used to deliver a biologically active agent to a tissue in a subject. The medical device described above or made by the method described above is placed proximate a tissue and the biologically active agent is released to the tissue. In a specific embodiment, the medical device is used to treat pain, specifically sciatica. The device is placed proximate an area to be treated, such as an area of pain or an area of origin of pain, such as a nerve. In one embodiment, one or more devices are implanted as a rod or series of rods proximate a site of pain or origination of pain (i.e., proximate a nerve).

When the medical device is a drug depot, in some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

The implant(s) can be placed proximate the tissue by any of several methods. In one embodiment, the medical device is delivered into the subject through a cannula, such as a needle. The benefit is that there is no incision or open surgery required, resulting in less trauma. In another embodiment, the medical device is delivered into the subject via an open incision. For treatments of maladies such as post operative pain, the medical device can be implanted after a surgery has been conducted. The medical device can be implanted after the surgery and prior to closing the surgical incision.

Once implanted in a subject under physiological conditions, the device will release the biologically active agent over a time period. For example, the implanted medical device release the biologically active agent so that less than 50% of the biologically active agent is eluted after 20, 30, 40, 50, 60, 70, 80 and even 90 days after the medical device is implanted in the subject. Specifically, less than 80% of the biologically active agent is eluted after 20, 30, 40, 50, 60, 70, 80, 90, 100, 110 and even 120 days after the medical device is implanted in the subject.

If the polymer and all other components of the medical device are biodegradable, the medical device may simply degrade or resorb into the subject, thus requiring no explantation. If the polymer or any other components of the medical device are biostable, explantation may be required after the biologically active agent has been delivered.

The present invention is illustrated by the following examples. It is to be understood that the particular examples, materials, amounts, and procedures are to be interpreted broadly in accordance with the scope and spirit of the invention as set forth herein.

EXAMPLES

Comparative Methods of Making Drug Loaded Pellets
Materials

Poly (d,l lactide-co-glycolide) having a 85:15 lactide to glycolide molar ratio (PLGA8515), an intrinsic viscosity of 0.70 and ester end capped polymer chain ends was purchased from Lakeshore Biomaterials (Birmingham, Ala.). Clonidine HCl was purchased from Spectrum Chemicals (Gardena, Calif.). Methanol and acetone were purchased from Sigma-Aldrich.

Example 1

Preparation of Spray Dried Clonidine HCl

Clondine HCl was dissolved in methanol to yield a 12% (w/w) solution. The solution was spray dried in a Buchi B-290

Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for an additional 24 hours at 70° C. and 15 mmHg vacuum.

Example 2

Preparation of Spray Dried Clondine HCl/PLGA8515

Clondine HCl and PLGA8515 were both separately dissolved in acetone to yield a 2% (w/w) solution. A mixture of 10% of the Clonidine HCl solution and 90% of the PLGA8515 solution was spray dried in the Buchi Spray Dryer. The processing parameters were set as follows: inlet temp. (60° C.), aspirator (80%), nitrogen inlet (50 mm), spray flow rate (80 mL/hr) and ultrasonic generator (0.8 watts). The spray dried powder was collected and dried for an additional 24 hours at 30° C. and 15 mmHg vacuum.

Example 3

Preparation of Melt Extruded Rods

Three formulations having different preparation methods for clonidine HCl were prepared for melt extrusion. The first formulation contained PLGA8515 ground into powder using a Retsch (Retsch GmbH, Germany) rotor mill with an 80 micrometer sieve filter and clonidine HCl used as received from the manufacturer. The second formulation contained ground PLGA8515 and spray dried clonidine HCl from Example 1. The third formulation contained spray dried clondine HCl/PLGA8515 from Example 2. Each formulation contained 10% (w/w) clonidine HCl and 90% (w/w) PLGA8515. The formulations were dry mixed with a spatula prior to being fed into a Haake Mini-Lab twin screw extruder (Thermo Fischer Scientific, Waltham, Mass.) set at 120° C. and 30 RPM. The rods were extruded out of a 0.75 mm diameter die.

Microscopy Analysis

TOF-SIMS data acquisition was performed on the rods of Example 3 using a ULVAC-PHI TRIFT III instrument (Chanhassen Minn.). During analysis, the instrument employed a mass filtered 22 keV Au$^+$ liquid metal ion source which was operated at 600 pA DC. The primary ion beam was pulsed at 11 kHz frequency with a pulse width of 12 ns. The total dose of primary ions was maintained below the static limit of $10^{13}$ ions/cm$^2$; therefore, the analysis depth was <2 nm. Low energy electrons were used for charge compensation by flooding the surface. Positive and negative ion "raw" data files were acquired for all samples. The outer surface of each rod was analyzed directly. The cross-section of each rod was also analyzed after cutting through it with a razor blade.

Example 4

In-Vitro Drug Elution Testing

The rods from Example 3 were cut with a razor blade to lengths of 1 mm length by ~1 mm diameter. 20 mg of pellets were placed in 20 mL scintillation vials for drug elution testing. The pellets were incubated in 10 mL of phosphate buffered saline pH 7.4 (Hyclone, 0.0067M) at 37° C. under mild agitation. At pre-selected times, the buffer was removed for analysis and replaced with fresh buffer medium. The drug content was quantified at 226 nm by a Molecular Devices SpectraMax M2 (Sunnyvale, Calif.) plate reader.

Results

Figure 2:
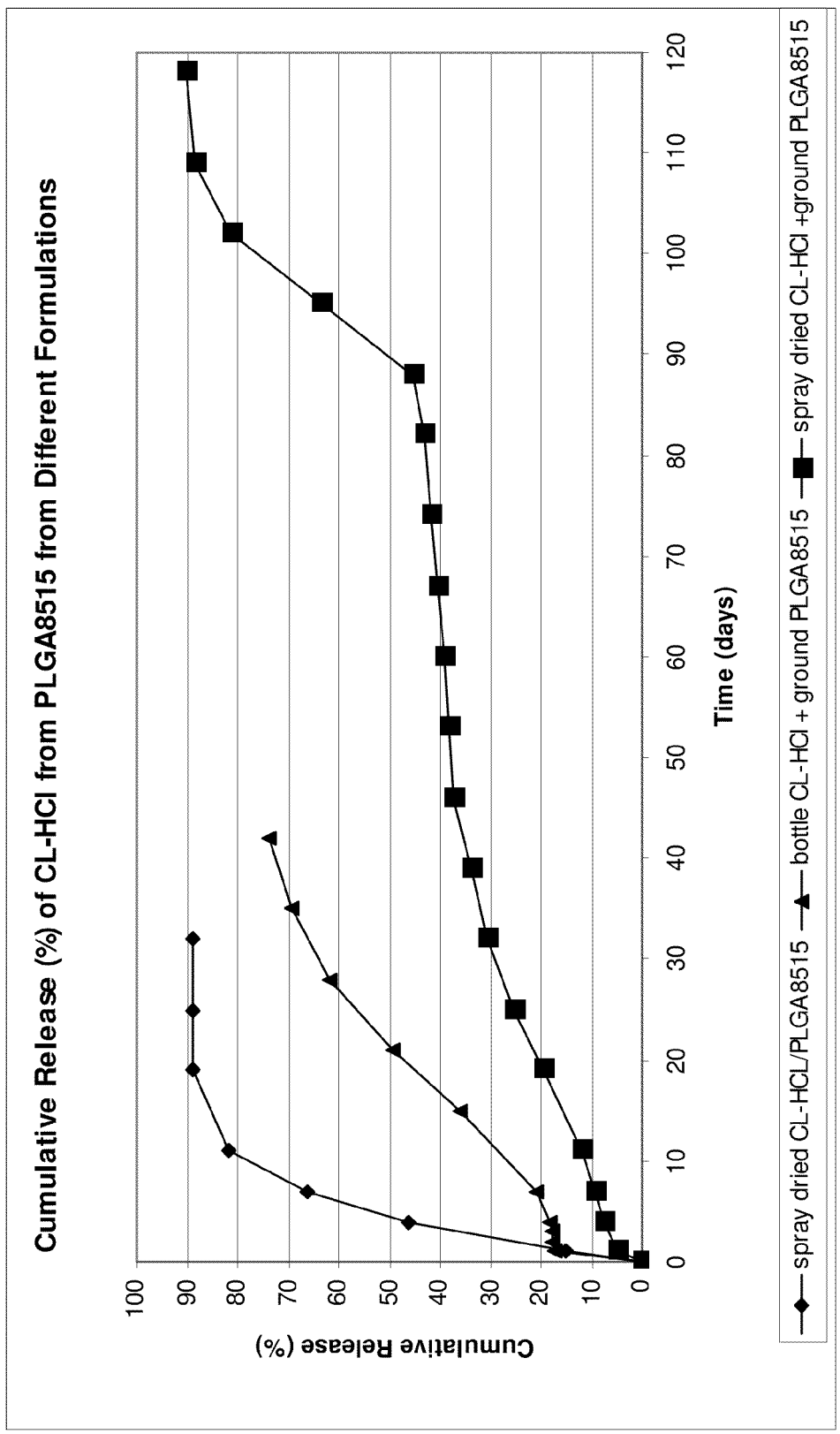
FIG. 2 is a graph comparing the in vitro release rates of clonidine HCl from PLGA pellets from an implantable medical device prepared three different ways as described in Example 4. The first formulation from Example 3, containing PLGA8515 ground into powder and clonidine HCl used as received from the manufacturer is represented by triangles, the second formulation, containing ground PLGA8515 and spray dried clonidine HCl from Example 1, is represented by squares, and the third formulation, containing spray dried clondine HCl/PLGA8515 from Example 2, is represented by diamonds.

FIG. 2 shows a comparison of the in-vitro elution rates of clonidine HCl from PLGA8515 pellets containing drug prepared in Example 3. The first formulation from Example 3, containing PLGA8515 ground into powder and clonidine HCl used as received from the manufacturer is represented by triangles. The drug depot or device releases clonidine over a period of 40 days, releasing about 5 to 10% of its drug load every 10 days or about 0.25% to 2% of its drug load on a daily basis. 70% of the drug is released from the drug depot in 40 days. % Cumulative release (also known as % theoretical drug eluted) is the measured amount of drug released as a measure of weight divided by the theoretical weight. Thus the drug depot is weighed on day zero and then days subsequent to obtain the % cumulative release as indicated in the graph.

The first formulation that was spray dried and the polymer was not subjected to subsequent grinding. The elution profile is represented by the diamonds. This formulation had a more rapid release rate than the second formulation as some particles were spherical and the particle sizes of the first are smaller than 100 microns in size when compared to the second formulation. The second formulation, containing ground PLGA8515 and spray dried clonidine HCl from Example 1, is represented by squares. The drug depot or device releases clonidine over a period of about 120 days, releasing about 5 to 10% of its drug load per every 10 days or about 0.25% to 2% of its drug load on a daily basis. The release is very consistent over about 20 to 90 days where about 40% of the drug is released. The drug depot releases 90% of the drug from the drug depot over 120 days. The grounding of the polymer allows production of more irregular shaped particles. Some particle sizes in the second formulation were larger than 100 microns and this formulation had, in general, a slower release than the first and third formulations. This is surprising as one would, in general, consider that the larger particles would go into solution first and thus there would be a rapid release of drug from the polymer. Here the larger particles prolong the release. The third formulation, containing spray dried clonidine HCl/PLGA8515 (no grinding) from Example 2, is represented by diamonds. This drug depot has a more rapid release profile where 90% of the drug is released within 30 days as compared to the first and second formulations. The drug depot has a bolus effect as well, where up to about 45% of the drug is released from the depot within 5 days.

These formulations had the drug uniformly distributed in the polymer matrix. It has been found that by controlling the particle size distribution of the drug powder, the drug distribution within the polymer matrix is more uniform and can be controlled.

Figure 3:
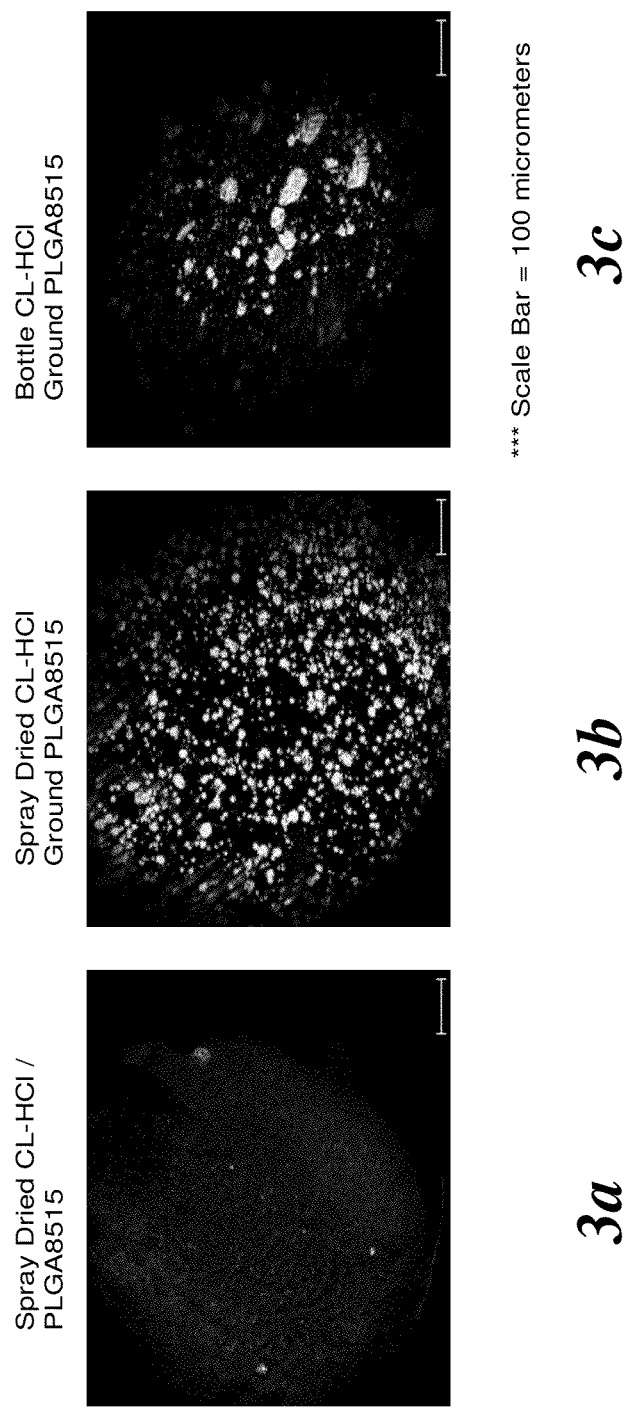
FIGS. 3a, 3b and 3c show the drug distribution within the polymer pellets analyzed by ToF-SIMS as described in Example 3.

FIGS. 3a, 3b and 3c show the drug distribution within the polymer pellets analyzed by ToF-SIMS as described in Example 3. FIG. 3a represents the formulation from Example 3 containing spray dried clonidine HCl/PLGA (no grinding) as described in Example 2. FIG. 3b represents the formulation from Example 3 containing spray dried clonidine HCl as described in Example 1 and PLGA ground into powder. FIG. 3c represents the formulation from Example 3 containing PLGA ground into powder and clonidine HCl used as received from the manufacturer. Comparison of the drug release rate shown in FIG. 2 and drug distribution as seen in FIGS. 3a, 3b and 3c demonstrate the effect of drug particle size on release. Each slide shows uniform distribution throughout the polymer as there are no voids or pockets showing only polymer. The small drug particles found in the pellets with spray dried Clonidine-HCl/PLGA8515 as seen in FIG. 3a, released the drug the fastest, while the formulation where the drug was spray dried and had ground polymer and larger size drug particles (as compared to 3a) as shown in FIG. 3b, released the drug over the longest period of time. Spray drying processing allows for some of the particles to be in spherical shape, while ground processing allows for some of the particles to be irregular shape or rough surfaces. The formulation with the larger particle size (indicated as bottle in FIG. 2) released slower than the spray dried formulation (without ground polymer). This is surprising, as one would consider that as the larger particles go into solution, there would be a more rapid release of drug from the polymer.

The formulation using clonidine-HCl directly from the manufacturer, shown in FIG. 3c, had some very large drug particles (>100 micrometers) and a large particle size distribution (5-150 micrometers) as determined by analysis of the image. The two spray dried formulations had very tight particle size distributions. The spray dried clonidine-HCl/PLGA8515 formulation had a particle size distribution of the drug between about 1-5 micrometers as determined by analysis of the image (FIG. 3a). The spray dried clonidine-HCl ground PLGA8515 formulation had a particle size distribution of the drug between about 10-20 micrometers as determined by analysis of the image (FIG. 3b). The spray dried formulation having a larger particle size had a slower drug release rate from the polymer. This is surprising, as one would consider that as the larger particles go into solution, there would be a more rapid release of drug from the polymer.

The optimal drug particle size range of a 10% (w/w) clonidine HCl formulation for controlled long-term drug release was determined to be 10-20 micrometers. The formulation had the lowest day one drug burst and a long duration of drug release as compared to the other formulations Comparative Formulations of Drug Loaded Pellets
Materials Poly (d,l lactide-co-glycolide) having a 85:15 lactide to glycolide molar ratio (PLGA8515), an intrinsic viscosity of 0.70 and ester end capped polymer chain ends was purchased from Lakeshore Biomaterials. Poly (d,l lactide) (PLA) having an intrinsic viscosity of 0.76 and ester end capped polymer chain ends was also obtained from Lakeshore Biomaterials. Spray dried clonidine HCl was prepared in a similar fashion as described in Example 1.

Example 5

Preparation of Melt Extruded Rods

Three formulations having clonidine HCl drug loadings of 5% (w/w), 10% (w/w), and 20% (w/w) were prepared for melt extrusion with PLGA8515 and for melt extrusion with PLA (six total formulations). Each formulation contained polymer ground into powder using a Retsch (Retsch GmbH, Germany) rotor mill with an 80 micrometer sieve filter and spray dried clonidine HCl as described above in Example 1. All formulations were dry mixed with a spatula prior to being fed into a Haake Mini-Lab twin screw extruder (Thermo Fischer Scientific, Waltham, Mass.) set at 120° C. and 30 RPM. The rods were extruded out of a 0.75 mm diameter die and pulled by hand to obtain a final diameter of ~0.7-0.8 mm.
Microscopy Analysis TOF-SIMS data acquisition was performed on the materials from Example 5 using a ULVAC-PHI TRIFT III instrument (Chanhassen Minn.). During analysis, the instrument employed a mass filtered 22 keV Au$^+$ liquid metal ion source which was operated at 600 pA DC. The primary ion beam was pulsed at 11 kHz frequency with a pulse width of 12 ns. The total dose of primary ions was maintained below the static limit of $10^{13}$ ions/cm$^2$; therefore, the analysis depth was <2 nm. Low energy electrons were used for charge compensation by flooding the surface. Positive and negative ion "raw" data files were acquired for all samples. The outer surface of each rod was analyzed directly. The cross-section of each rod was also analyzed after cutting through it with a razor blade.

Example 6

In-Vitro Drug Elution Testing

Figure 4:
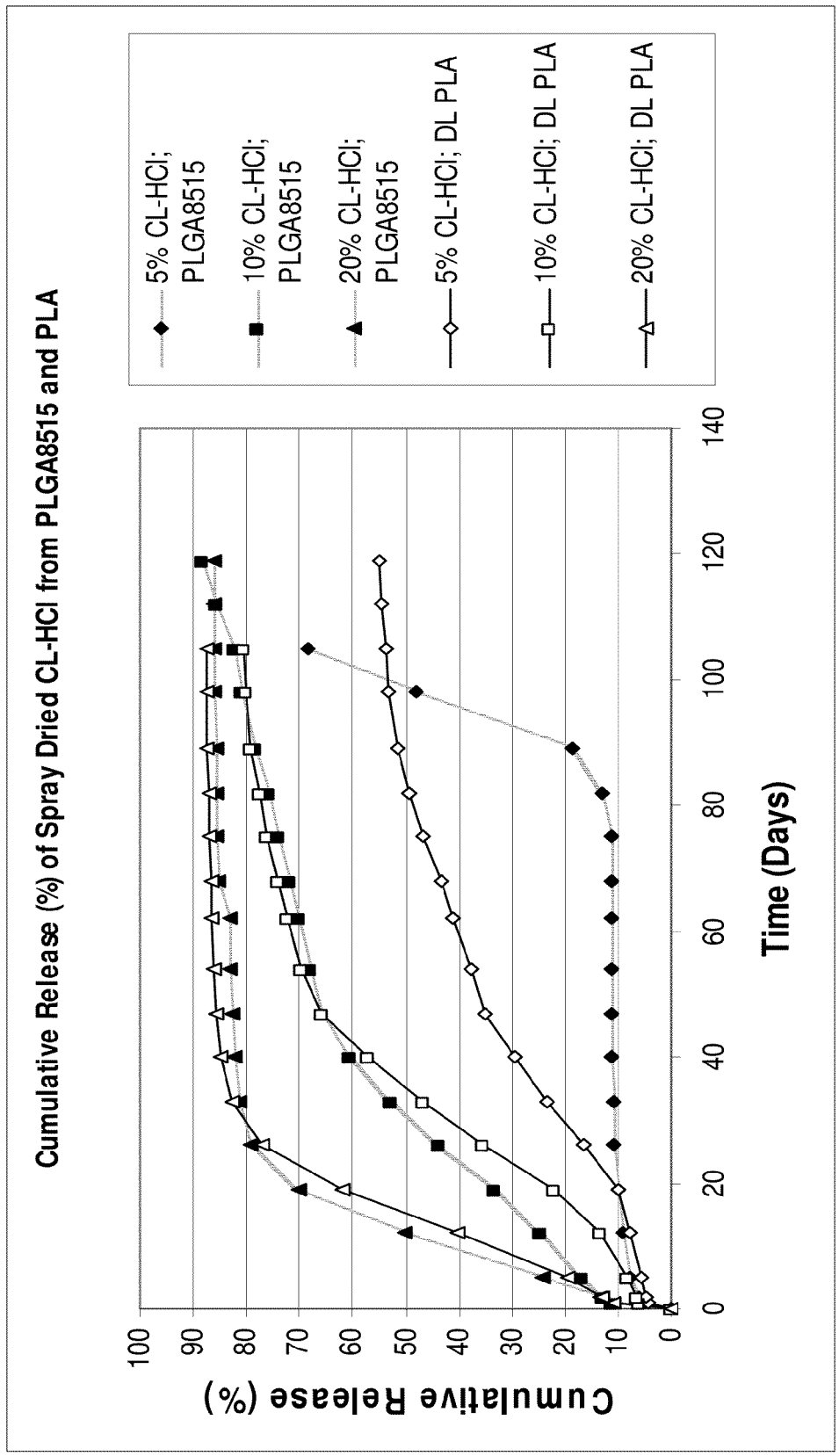
FIG. 4 is a graph comparing the in vitro release rates of clonidine HCl from the pellets containing drug prepared in Example 5. The formulations from Example 5 containing PLGA8515 as the carrier polymer are represented by white data points, and the formulations from Example 5 containing PLA as the carrier polymer are represented by black data points. The formulations containing 20% loading of clonidine HCL are represented by triangles, the formulations containing 10% loading of clonidine HCL are represented by squares, and the formulations containing 5% loading of clonidine HCL are represented by diamonds.

The rods from Example 5 were cut with a razor blade to lengths of 0.75 mm, 1.5 mm and 3.0 mm length depending on the corresponding drug loadings of 20%, 10% and 5%. 10 pellets from each formulation were placed in 20 mL scintillation vials for drug elution testing. The pellets were incubated in 5 mL of phosphate buffered saline pH 7.4 (Hyclone, 0.0067M) at 37° C. under mild agitation. At pre-selected times, the buffer was removed for analysis and replaced with fresh buffer medium. The drug content was quantified at 226 nm by a Molecular Devices SpectraMax M2 (Sunnyvale, Calif.) plate reader.
Results FIG. 4 shows a comparison of the in-vitro elution rates of clonidine HCl from the pellets containing drug prepared in Example 5. The formulations from Example 5 containing PLGA8515 as the carrier polymer are represented by white data points, and the formulations from Example 5 containing PLA as the carrier polymer are represented by black data points. The formulations containing 20% loading of clonidine HCL are represented by triangles, the formulations containing 10% loading of clonidine HCL are represented by squares, and the formulations containing 5% loading of clonidine HCL are represented by diamonds.

The formulation containing 20% clonidine HCl in DL PLA or 20% clonidine in PLGA8515 released about 90% of the clonidine over a period of about 120 days, releasing about 20% within the first few days and then about 80% over 20 days. The release is very linear or consistent over about 30 to 120 days. The high drug load (20%) caused more drug to be released from the depot over the measured time period.

The formulation containing 10% clonidine HCl in DL PLA or 10% clonidine in PLGA8515 released about 85% of the clonidine over a period of about 120 days, releasing about 10-15% within the first few days and then about 60% over 40 days. The release is linear or consistent over about 60 to 120 days. The drug load of 10% caused less drug to be released from the depot over the measured time period as compared to 20% drug loads.

The formulation containing 5% clonidine HCl in PLGA8515 released about 70% of the clonidine over a period of about 100 days, releasing about 10% within the first few days and then about 12% to 70% on day 80 to 100. The drug load of 5% caused less drug to be released from the depot over the measured time period as compared to 10% or 20% drug loads. The formulation containing 5% clonidine HCl in DL PLA released about 55% of the clonidine over a period of about 120 days, releasing about 5% within the first few days and then about 5% to about 10% every 5 to 10 days. The drug load of 5% caused less drug to be released from the depot over the measured time period as compared to 10% or 20% drug loads and there was a gradual rise in release as compared to the spike starting at day 90 for the 5% clonidine PLGA 8515 formulation.

Figure 5:
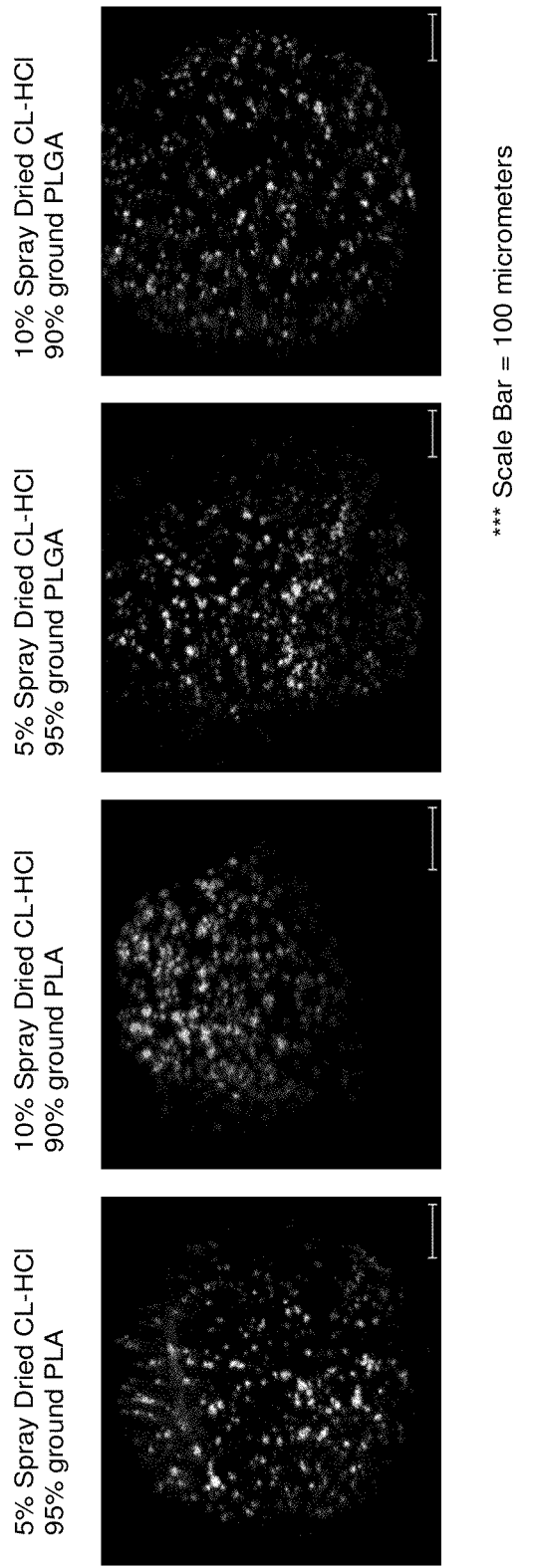
FIGS. 5a, 5b, 5c and 5d show the drug distribution within the polymer pellets analyzed by ToF-SIMS as described in Example 5.

FIGS. 5a, 5b, 5c and 5d show the drug distribution within the polymer pellets or drug depots analyzed by ToF-SIMS as described in Example 5. FIG. 5a represents the formulation containing 5% clonidine HCl and 95% PLA, FIG. 5b represents the formulation containing 10% clonidine HCl and 90% PLA, FIG. 5c represents the formulation containing 5% clonidine HCl and 95% PLGA8515, and FIG. 5d represents the formulation containing 10% clonidine HCl and 90% PLGA8515. Comparison of the drug release rate shown in FIG. 4 and drug distribution as seen in FIGS. 5a, 5b, 5c and 5d demonstrate that spray dried drug was well distributed within all of the polymer matrices, indicating that polymer composition has little to no dependence on the distribution of the drug. As is the case in Example 4, the drug particle sizes within the polymer matrices were roughly 10-20 micrometers in diameter as determined by analysis of the image. The elution and imaging results demonstrate how tunable the drug release is by changing the drug loading and or polymer composition. The particles were uniformly distributed throughout the polymer. Spray drying processing allows for some of the particles to be in spherical shape.

Example 7

Materials
Poly (d,l lactide) having an intrinsic viscosity of 0.76 and ester end capped polymer chain ends was also obtained from Lakeshore Biomaterials. Clonidine HCl was obtained from Spectrum Chemicals and jet milled at Micron Technologies (Exton, Pa.) to various particles sizes. The jet milled Clonidine HCl was then sieved to final particle sizes of 10-50 micrometers and <5 micrometers.
Methods
Preparation of Melt Extruded Rods
Four formulations having clonidine HCl drug loadings of 5% (w/w), 10% (w/w) and drug particles sizes of 10-50 micrometers and <5 micrometers were prepared for melt extrusion with PLA. Each formulation contained polymer ground into powder using a Retsch (Retsch GmbH, Germany) rotor mill with an 80 micrometer sieve filter and jet milled clonidine HCl. All formulations were dry mixed with a spatula prior to being fed into a Haake Mini-Lab twin screw extruder (Thermo Fischer Scientific, Waltham, Mass.) set at 120° C. and 30 RPM. The rods were extruded out of a 0.50 mm diameter die and pulled by hand to obtain a final diameter of ~0.5-0.6 mm.
Microscopy Analysis
The morphologies of the drug loaded rods are assessed by scanning electron micrographs (SEM) of microtomed samples. For sample preparation, the rods are cooled to 6 degrees C and cut with either a glass or diamond blade (Microstar MS1 Cryo Ultramicrotome, Huntsville, Tex.). The microtomed face of the rod is then sputter coated with Au and Pd to create a conductive surface for SEM imaging. The SEM (JEOL JSM-5900LV, Peabody, Mass.) is run at 10 kV, and multiple micrographs of various magnifications are acquired. An overview captures the entire rod, allowing for evaluation of macro features. Other higher magnification images are acquired to reveal finer features of the sample. Backscatter Imaging has proved to be most useful when imaging this system as the Cl containing drug has a significant contrast from the lower atomic weight polymer.
In-Vitro Drug Elution Testing
The rods were cut with a razor blade to lengths of 4 mm and placed in 20 mL scintillation vials for drug elution testing. The pellets were incubated 1.7 mL of phosphate buffered saline pH 7.4 (Hyclone, 0.00067M) at 37° C. under mild agitation. At pre-selected times, the buffer was removed for analysis and replaced with fresh buffer medium. The drug content was quantified at 226 nm by a Molecular Devices SpectraMax M2 (Sunnyvale, Calif.) plate reader.
Drug Particle Sizing
Clonidine HCl was suspended in acetone to yield a cloudy suspension (~10 mg/4 mL). The suspension was pipetted into the fraction cell holder for the Horiba Instruments Partica LA-950 Laser Difraction Particle Size Analyzer until the % transmittance reached 80-90%.

Figure 6:
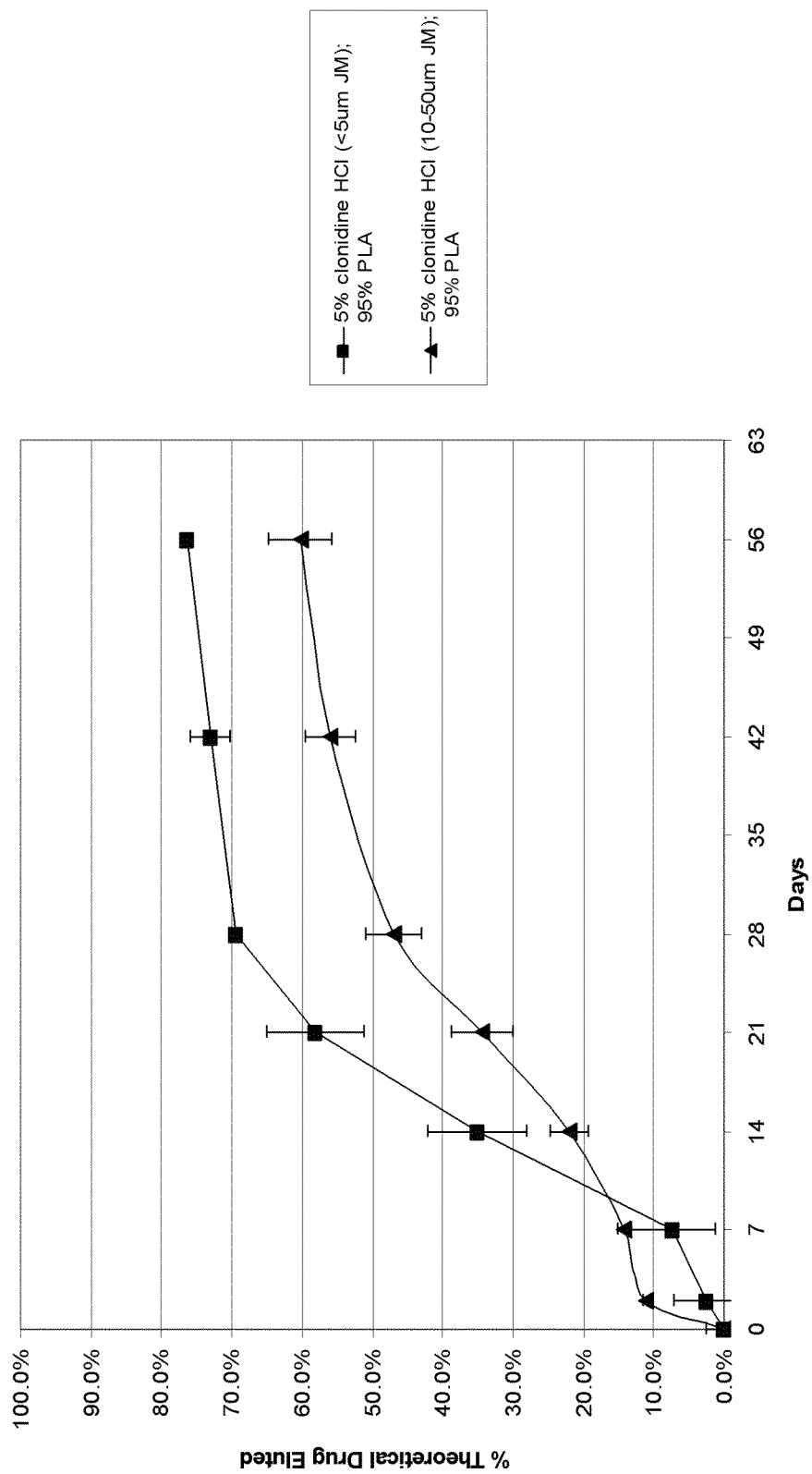
FIG. 6 is a graph comparing the in vitro release rates of clonidine HCl from the pellets containing drug prepared in Example 7. The formulation from Example 7 containing 95% PLA as the carrier polymer and 5% clonidine HCL having a particle size of less than 5 micrometers is represented by squares. The formulation from Example 7 containing 95% PLA as the carrier polymer and 5% clonidine HCL having a particle size of between 10 microns to 500 microns is represented by triangles.

FIG. 6 is a graph comparing the in vitro release rates of clonidine HCl from the pellets containing drug prepared in Example 7. The formulation from Example 7 containing 95% PLA as the carrier polymer and 5% clonidine HCL having a particle size of less than 5 micrometers is represented by squares. The clonidine particles were jet milled so they had random shapes (e.g., some irregular surface particles, some smooth particles). This formulation had clonidine particles, which were very small and had a size of less than 5 micrometers, which allowed a rapid release of the drug from the polymer. About 10% of the drug was released within 7 days and about 35% of the drug was released in 14 days and about 60% of the drug was released in 21 days and about 70% of the drug in 28 days. There was about linear release from day 28 to day 56. Almost 80% of the drug was released from the polymer during the 56 days. In general, the small particles size caused more rapid release of the drug from the polymer (e.g., depot) over the measured time period as compared to the larger particle size of 10 micrometers to 50 micrometers.

The formulation from Example 7 containing 95% PLA as the carrier polymer and 5% clonidine HCL having a particle size of between 10 microns to 50 microns is represented by triangles. The clonidine particles were jet milled so they had random shapes (e.g., some irregular surface particles, some smooth particles). This formulation having clonidine particles were small—about 10 micrometers to 50 micrometers, which allowed a rapid release of the drug from the polymer, but not as rapid a release as the less than 5 micrometer formulation. About 15% of the drug was released within 2 days and about 20% of the drug was released in 14 days and about 35% of the drug was released in 21 days and about 45% of the drug in 28 days. There was about linear release from day 42 to day 56. About 60% of the drug was released from the polymer in 56 days. In general, the larger particles size caused slower release of the drug from the polymer (e.g., depot) over the measured time period as compared to the very small particle size of less than 5 micrometers of the other formulation.

Figure 7:
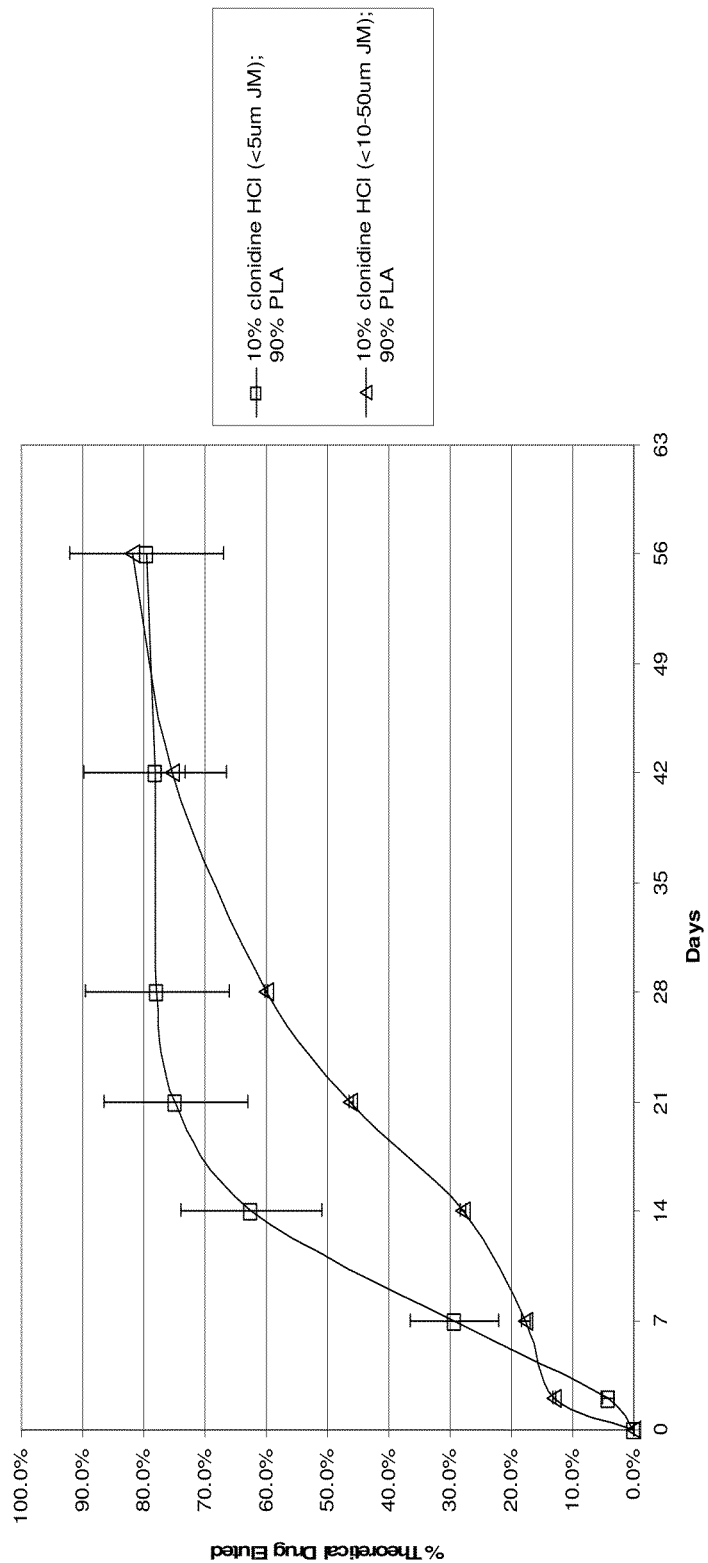
FIG. 7 is a graph comparing the in vitro release rates of clonidine HCl from the pellets containing drug prepared in Example 7. The formulation from Example 7 containing 90% PLA as the carrier polymer and 10% clonidine HCL having a particle size of less than 5 micrometers is represented by open squares. The formulation from Example 7 containing 90% PLA as the carrier polymer and 10% clonidine HCL having a particle size of between 10 micrometers to 500 micrometers is represented by open triangles.

FIG. 7 is a graph comparing the in vitro release rates of clonidine HCl from the pellets containing drug prepared in Example 7. The formulation from Example 7 containing 90% PLA as the carrier polymer and 10% clonidine HCL having a particle size of less than 5 micrometers is represented by open squares. The clonidine particles were jet milled so they had random shapes (e.g., some irregular surface particles, some smooth particles). This formulation had 10% clonidine load and very small clonidine particles having a size of less than 5 micrometers, which allowed a rapid release of the drug from the polymer over a shorter period of time when compared to the formulations in FIG. 6. About 10% of the drug was released within 3 days and about 30% of the drug was released in 7 days and about 62% of the drug was released in 14 days and about 80% of the drug in 28 days. There was about linear release from day 28 to day 56. About 80% of the drug was released from the polymer in 56 days. In general, the small particles size caused rapid release of the drug from the polymer (e.g., depot) over the measured time period as compared to the larger particle size of 10 micrometers to 50 micrometers.

The formulation from Example 7 containing 90% PLA as the carrier polymer and 10% clonidine HCL having a particle size of between 10 micrometers to 50 micrometers is represented by open triangles. This formulation had 10% clonidine load and clonidine particles having a size of 10 micrometers to 50 micrometers, which allowed a rapid release of the drug from the polymer. About 12% of the drug was released within 2 days and about 30% of the drug was released in 14 days and about 60% of the drug was released in 28 days and about 80% of the drug in 56 days. There was about linear release from day 49 to day 56. In general, the larger particles size caused slower release of the drug from the polymer (e.g., depot) over the measured time period as compared to the very small particle size of less than 5 micrometers of the other formulation. This is surprising as one would consider that as the larger particles go into solution, there would be a more rapid release of drug from the polymer.

Figure 8:
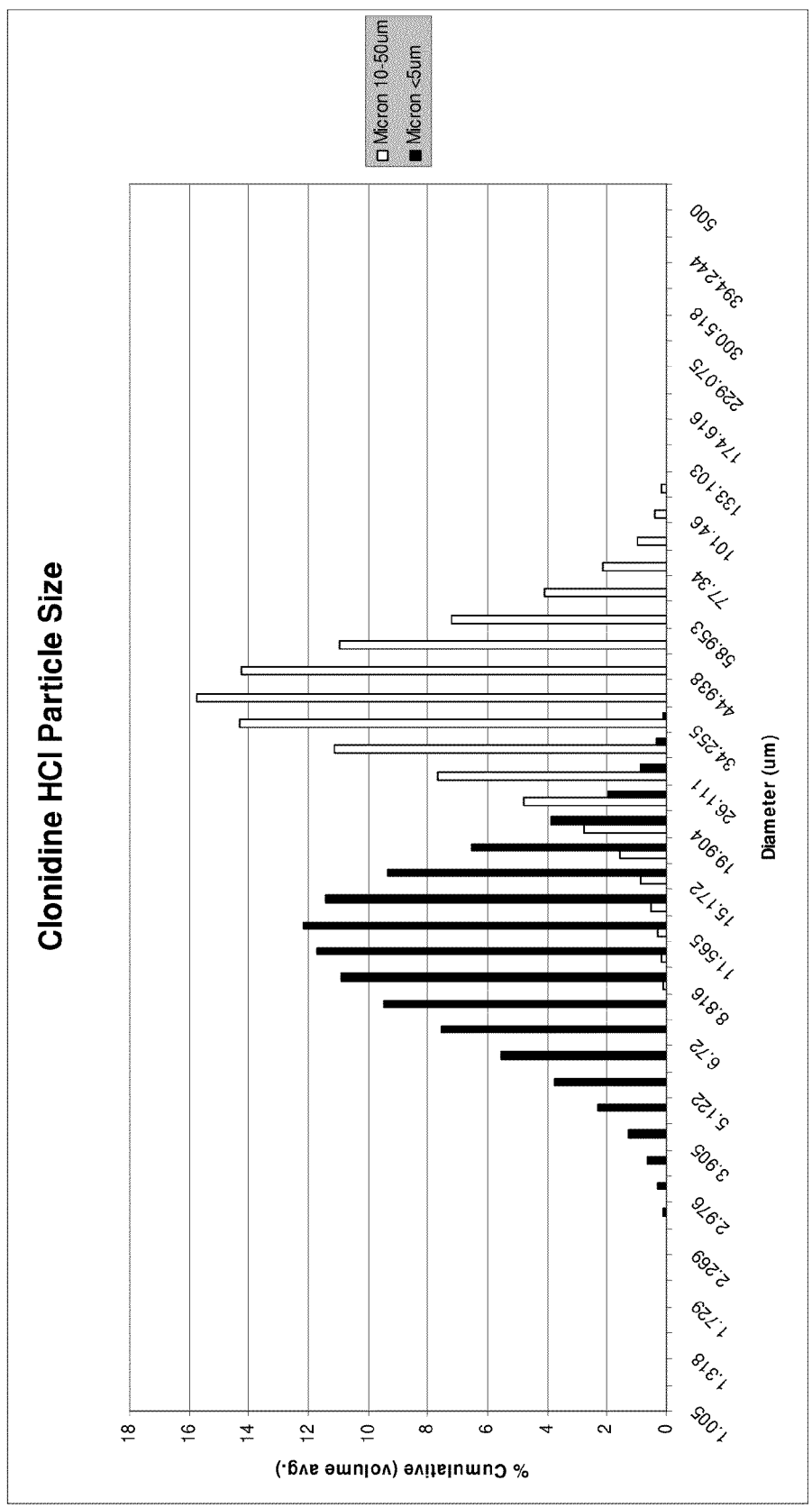
FIG. 8 illustrates a bar graph of particle size distribution for the formulation in Example 7 before polymer addition. Open bars are 10-50 micrometer size clonidine particles and shaded bars are less than 5 micrometer clonidine particle sizes.

FIG. 8 illustrates a bar graph of particle size distribution for the formulation in Example 7 before polymer addition. Open bars are 10-50 micrometer size clonidine particles and shaded bars are less than 5 micrometer clonidine particle sizes. The size of the particles remained within the range after polymer addition as shown in FIG. 9.

Figure 9:
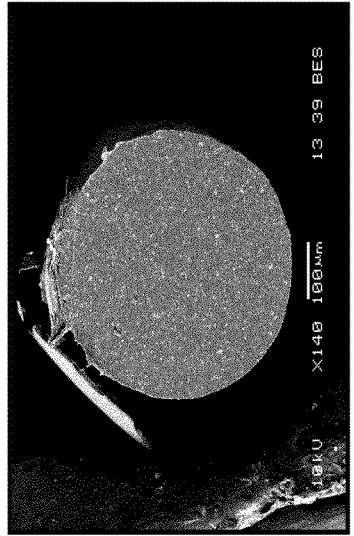
FIG. 9 shows the drug distribution within the polymer pellets made in Example 7 analyzed by scanning electron micrographs. Upper left panel represents the formulation containing 95% PLA as the carrier polymer and 5% clonidine HCL having a particle size of less than 5 micrometers. The lower left panel contains 95% PLA as the carrier polymer and 5% clonidine HCL having a particle size of between 10 micrometers to 50 micrometers. Upper right panel represents the formulation containing 90% PLA as the carrier polymer and 10% clonidine HCL having a particle size of less than 5 micrometers. The lower left panel contains 90% PLA as the carrier polymer and 5% clonidine HCL having a particle size of between 10 micrometers to 50 micrometers.
Figure 9:
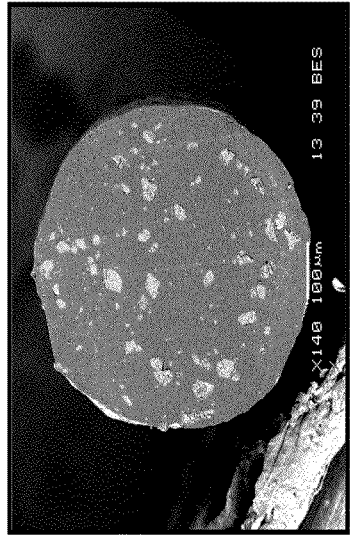
Figure 9:
Figure 9:
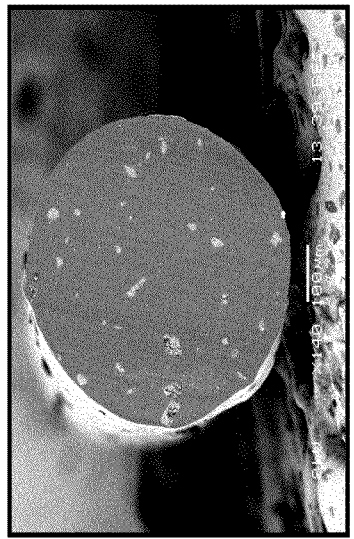

FIG. 9 shows the drug distribution within the polymer pellets made in Example 7 analyzed by scanning electron micrographs. Upper left panel represents the formulation containing 95% PLA as the carrier polymer and 5% clonidine HCL having a particle size of less than 5 micrometers. The lower left panel contains 95% PLA as the carrier polymer and 5% clonidine HCL having a particle size of between 10 micrometers to 50 micrometers. Upper right panel represents the formulation containing 90% PLA as the carrier polymer and 10% clonidine HCL having a particle size of less than 5 micrometers. The lower right panel contains 90% PLA as the carrier polymer and 10% clonidine HCL having a particle size of between 10 micrometers to 50 micrometers. Even after processing, the clonidine size difference of the different formulations remained consistent less than 5 micrometers and between 10-50 micrometers. The clonidine particles were uniformly distributed throughout the polymer.

Example 8

Comparative Methods of Making Drug Loaded Pellets
Drug Particle Sizing

Clonidine HCl was suspended in acetone to yield a cloudy suspension (~10 mg/4 mL). The suspension was pipetted into the fraction cell holder for the Horiba Instruments Partica LA-950 Laser Diffraction Particle Size Analyzer until the % transmittance reached 80-90%.

Figure 10:
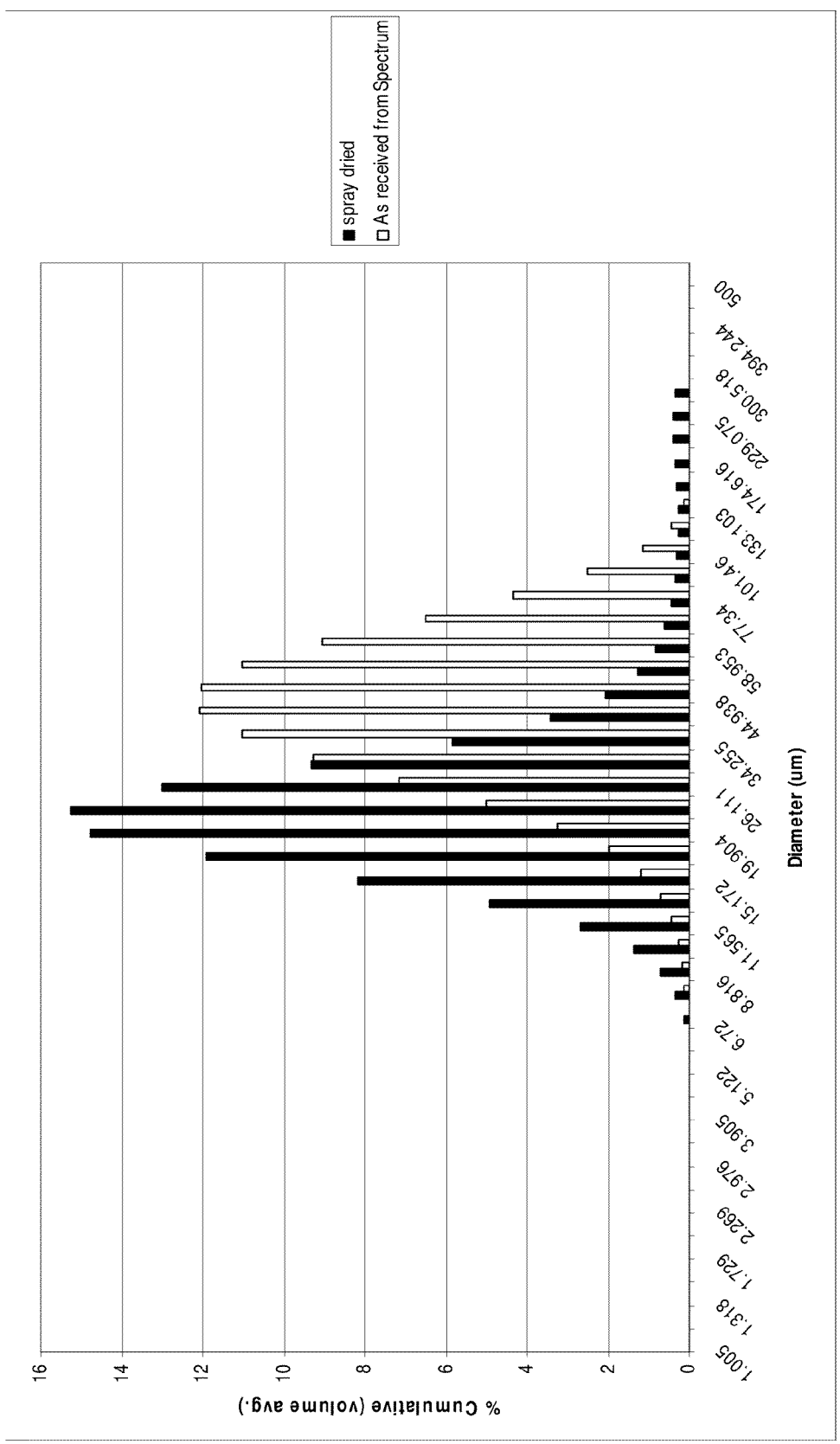
FIG. 10 illustrates a bar graph of clonidine particle size distribution for the formulation in Example 3 before the polymer addition and spray drying. Open bars are the clonidine particle size as received from the manufacturer used in the spray dried ground PLGA 8515 formulation and shaded bars are the particle sizes of the clonidine used in the spray dried ground PLGA 8515 formulation.

FIG. 10 illustrates a bar graph of clonidine particle size distribution for the formulation in Example 3 before the polymer addition. Open bars are the clonidine particle size as received from the manufacturer (indicated as "bottle" in FIG. 2) used in the spray dried ground PLGA 8515 formulation and shaded bars are the particle sizes of the clonidine used in the spray dried ground PLGA 8515 formulation.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. An implantable medical device in the shape of a pellet, rod, or cylinder, having a diameter between about 0.5 mm to about 1 mm, comprising:
    at least one biodegradable polymer having an average molecular weight of 50,000 to 100,000 and comprising poly(D,L-lactide-co-caprolactone) or poly(L-lactide-co-caprolactone) that is present in an amount from about 80-95% of the implantable medical device by weight; and
    at least one biologically active agent comprising clonidine hydrochloride wherein clonidine is present in an amount from about 5-15% of the implantable medical device by weight, wherein the clonidine hydrochloride is disposed homogeneously within the medical device as particles and at least 80% of the particles have a particle size between about 10 to about 20 micrometers,
    wherein the implantable medical device releases a bolus dose of clonidine hydrochloride in an amount of about 45% of the clonidine hydrochloride within 5 days of implantation and releases clonidine hydrochloride over up to 30 days.

2. The implantable medical device of claim 1, wherein the implantable medical device provides an elution profile wherein less than 80% of the biologically active agent is eluted after 60 days after the implantable medical device is implanted in a subject under physiological conditions.

3. The implantable medical device of claim 2, wherein the composition provides an elution profile wherein less than 80% of the biologically active agent is eluted after 100 days after the implantable medical device is implanted in a subject under physiological conditions.

4. The implantable medical device of claim 1, wherein the biologically active agent further comprises fluocinolone acetonide, dexamethasone or sulindac.

5. The implantable medical device of claim 1, wherein the polymer has an amorphous morphology and the biologically active agent has a crystalline morphology.

6. The implantable medical device of claim 1, wherein the implantable medical device is in the shape of a cylindrical rod.

7. The implantable medical device of claim 1, wherein the biologically active agent is present in an amount from about 8-12% by weight.

8. The implantable medical device of claim 1, wherein at least 90% of the biologically active agent particles have a particle size between 10-20 micrometers in diameter.

9. The implantable medical device of claim 1, wherein the implantable medical device is a drug depot for treating pain.

10. A drug depot in the shape of a pellet, rod, or cylinder, comprising:
    at least one biodegradable polymer having an average molecular weight of 50,000 to 100,000 and comprising poly(D,L-lactide-co-caprolactone) or poly(L-lactide-co-caprolactone) that is present in an amount from about 80-95% of the drug depot by weight, and
    clonidine hydrochloride in an amount from about 5-20% of the drug depot by weight, wherein the clonidine hydrochloride is disposed homogeneously within the drug depot as particles and at least 80% of the particles have a particle size between about 10 to about 20 micrometers, and wherein the drug depot releases a bolus dose of clonidine hydrochloride in an amount of about 45% of the clonidine hydrochloride within 5 days of implantation and releases clonidine hydrochloride over up to 30 days.

11. An implantable medical device according to claim 1, wherein the implantable medical device has a length of 3 mm.

12. An implantable medical device according to claim 1, wherein the implantable medical device has a length of 4 mm and a diameter of 0.5 mm.

13. A drug depot according to claim 10, wherein the drug depot has a length of 3 mm.

14. A drug depot according to claim 10, wherein the drug depot has a length of 4 mm and a diameter of 0.5 mm.

15. An implantable medical device according to claim 1, wherein the implantable medical device has a diameter of 0.75 mm.

16. A drug depot according to claim 10, wherein the drug depot has a diameter of 0.75 mm.

* * * * *